(12) United States Patent
Paty et al.

(10) Patent No.: US 8,380,531 B2
(45) Date of Patent: Feb. 19, 2013

(54) CLINICAL TRIAL ENDPOINT DEVELOPMENT PROCESS

(75) Inventors: Jean Paty, Pittsburgh, PA (US); Alan Shields, Johnson City, TN (US); Chad Gwaltney, Westerly, RI (US); Brian Tiplady, Edinburgh (GB)

(73) Assignee: Invivodata, Inc., Pittsburgh, PA (US)

( * ) Notice: Subject to any disclaimer, the term of this patent is extended or adjusted under 35 U.S.C. 154(b) by 323 days.

(21) Appl. No.: 12/509,318

(22) Filed: Jul. 24, 2009

(65) Prior Publication Data

US 2010/0023346 A1 Jan. 28, 2010

Related U.S. Application Data

(60) Provisional application No. 61/083,575, filed on Jul. 25, 2008.

(51) Int. Cl.
*G06Q 10/00* (2012.01)
*G06Q 50/00* (2012.01)

(52) U.S. Cl. ............................................. 705/2; 705/3

(58) Field of Classification Search .................. 705/2–3; 600/300
See application file for complete search history.

(56) References Cited

U.S. PATENT DOCUMENTS

| | | | |
|---|---|---|---|
| D247,251 S | 2/1978 | Napoli | |
| 4,262,632 A | 4/1981 | Hanton et al. | |
| 4,343,375 A | 8/1982 | Manning | |
| 4,353,375 A | 10/1982 | Colburn et al. | |
| 4,367,752 A | 1/1983 | Jimenez et al. | |
| 4,543,955 A | 10/1985 | Schroeppel | |
| 4,566,461 A | 1/1986 | Lubell et al. | |
| 4,592,018 A | 5/1986 | Wiegman | |
| 4,686,624 A | 8/1987 | Blum et al. | |
| 4,803,625 A | 2/1989 | Fu et al. | |
| 4,844,076 A | 7/1989 | Lesho et al. | |
| 4,883,063 A | 11/1989 | Bernard et al. | |
| 4,909,260 A | 3/1990 | Salem et al. | |
| 4,918,627 A | 4/1990 | Garcia et al. | |
| 4,966,154 A | 10/1990 | Cooper et al. | |
| 4,974,601 A | 12/1990 | Tranjan et al. | |
| 4,975,842 A | 12/1990 | Darrow et al. | |
| 4,987,897 A | 1/1991 | Funke | |
| 5,002,064 A | 3/1991 | Allain et al. | |
| 5,063,937 A | 11/1991 | Ezenwa et al. | |
| 5,078,134 A | 1/1992 | Heilman et al. | |
| 5,111,818 A | 5/1992 | Suzuki et al. | |

(Continued)

FOREIGN PATENT DOCUMENTS

| EP | 299667 A1 | 1/1989 |
|---|---|---|
| EP | 1034734 A1 | 3/2000 |

(Continued)

OTHER PUBLICATIONS

Shingo et al., Correlation of airway obstruction and patient-reported endpoints in clinical studies, 2001, European Respiratory Journal, pp. 220-224.*

(Continued)

*Primary Examiner* — Luke Gilligan
(74) *Attorney, Agent, or Firm* — Wilson Sonsini Goodrich & Rosati

(57) ABSTRACT

A system for developing and producing clinical endpoints based on patient reported outcome data utilizing algorithms to generate decision rules to evaluate patient reported outcome type questionnaire is provided. The questionnaires can include health-related quality of life questionnaires and can predict the reliability of endpoints in supporting one or more medical labeling claims.

53 Claims, 2 Drawing Sheets

U.S. PATENT DOCUMENTS

| | | | |
|---|---|---|---|
| 5,113,859 A | 5/1992 | Funke | |
| 5,128,552 A | 7/1992 | Fang et al. | |
| 5,131,390 A | 7/1992 | Sakaguchi et al. | |
| 5,137,345 A | 8/1992 | Waldorf et al. | |
| 5,181,519 A | 1/1993 | Bible | |
| 5,197,489 A | 3/1993 | Conlan | |
| 5,199,439 A | 4/1993 | Zimmerman et al. | |
| 5,213,106 A | 5/1993 | Lerner | |
| 5,213,555 A | 5/1993 | Hood et al. | |
| 5,218,969 A | 6/1993 | Bredesen et al. | |
| 5,222,503 A | 6/1993 | Ives et al. | |
| 5,226,424 A | 7/1993 | Bible | |
| 5,226,539 A | 7/1993 | Cheng | |
| 5,228,450 A | 7/1993 | Sellers | |
| 5,253,654 A | 10/1993 | Thomas et al. | |
| 5,261,412 A | 11/1993 | Butterfield et al. | |
| 5,271,405 A | 12/1993 | Boyer et al. | |
| 5,275,159 A | 1/1994 | Griebel | |
| 5,280,429 A | 1/1994 | Withers | |
| 5,289,824 A | 3/1994 | Mills et al. | |
| 5,307,262 A | 4/1994 | Ertel | |
| 5,307,263 A | 4/1994 | Brown | |
| 5,412,769 A | 5/1995 | Maruoka et al. | |
| 5,447,164 A | 9/1995 | Shaya et al. | |
| 5,454,376 A | 10/1995 | Stephens et al. | |
| 5,479,339 A | 12/1995 | Miller | |
| 5,547,878 A | 8/1996 | Kell | |
| 5,583,831 A | 12/1996 | Churchill et al. | |
| 5,596,994 A | 1/1997 | Bro | |
| 5,652,146 A | 7/1997 | Kell | |
| 5,671,734 A | 9/1997 | Pugh | |
| 5,672,154 A | 9/1997 | Sillen et al. | |
| 5,704,366 A | 1/1998 | Tacklind et al. | |
| 5,710,551 A | 1/1998 | Ridgeway | |
| 5,732,709 A | 3/1998 | Tacklind et al. | |
| 5,778,882 A | 7/1998 | Raymond et al. | |
| 5,832,448 A | 11/1998 | Brown | |
| 5,960,403 A | 9/1999 | Brown | |
| 5,963,136 A | 10/1999 | O'Brien | |
| 5,980,429 A | 11/1999 | Nashner | |
| 6,029,144 A | 2/2000 | Barrett et al. | |
| 6,039,688 A | 3/2000 | Douglas et al. | |
| 6,051,029 A | 4/2000 | Paterson et al. | |
| 6,063,028 A | 5/2000 | Luciano | |
| 6,075,755 A | 6/2000 | Zarchan | |
| 6,095,985 A | 8/2000 | Raymond et al. | |
| 6,151,586 A | 11/2000 | Brown | |
| 6,165,142 A | 12/2000 | Bar | |
| 6,167,362 A | 12/2000 | Brown et al. | |
| 6,171,237 B1 | 1/2001 | Avitall et al. | |
| 6,317,731 B1 | 11/2001 | Luciano | |
| 6,338,039 B1 | 1/2002 | Lonski et al. | |
| 6,381,577 B1 | 4/2002 | Brown | |
| 6,514,200 B1 | 2/2003 | Khouri | |
| 6,663,846 B1 | 12/2003 | Mccombs et al. | |
| 6,687,190 B2 | 2/2004 | Momich et al. | |
| 6,827,670 B1 | 12/2004 | Stark et al. | |
| 6,865,519 B2 | 3/2005 | Lampert et al. | |
| 6,879,970 B2 | 4/2005 | Shiffman et al. | |
| 6,895,405 B1 | 5/2005 | Choi et al. | |
| 6,996,560 B1 | 2/2006 | Choi et al. | |
| 7,054,782 B2 | 5/2006 | Hartlaub | |
| 7,058,517 B1 | 6/2006 | Denton et al. | |
| 7,072,802 B2 | 7/2006 | Hartlaub | |
| 7,124,059 B2 | 10/2006 | Wetzer et al. | |
| 7,185,065 B1 | 2/2007 | Holtzman et al. | |
| 7,249,043 B1 | 7/2007 | Trout et al. | |
| 7,251,609 B1 | 7/2007 | Mcalindon et al. | |
| 7,251,620 B2 | 7/2007 | Walker et al. | |
| 7,343,337 B1 | 3/2008 | Cieliebak et al. | |
| 7,415,447 B2 | 8/2008 | Shiffman et al. | |
| 7,840,393 B1 | 11/2010 | Whirley et al. | |
| 7,873,589 B2 | 1/2011 | Shiffman et al. | |
| 2001/0044408 A1 | 11/2001 | Reitberg | |
| 2002/0013516 A1 | 1/2002 | Reyre et al. | |
| 2002/0019748 A1 | 2/2002 | Brown | |
| 2002/0042726 A1 | 4/2002 | Mayaud | |
| 2002/0052858 A1 | 5/2002 | Goldman et al. | |
| 2002/0064095 A1 | 5/2002 | Momich et al. | |
| 2002/0082886 A1 | 6/2002 | Manganaris et al. | |
| 2002/0099570 A1 | 7/2002 | Knight | |
| 2002/0120471 A1 | 8/2002 | Drazen | |
| 2002/0143563 A1 | 10/2002 | Hufford et al. | |
| 2002/0143595 A1 | 10/2002 | Frank et al. | |
| 2002/0156640 A1 | 10/2002 | Hufford et al. | |
| 2003/0036683 A1 | 2/2003 | Kehr et al. | |
| 2003/0178031 A1 | 9/2003 | Du Pen et al. | |
| 2003/0194704 A1 | 10/2003 | Penn et al. | |
| 2004/0024639 A1 | 2/2004 | Goldman | |
| 2004/0122701 A1 | 6/2004 | Dahlin et al. | |
| 2005/0009862 A1 | 1/2005 | Sabounjian et al. | |
| 2005/0154676 A1 | 7/2005 | Ronning et al. | |
| 2005/0165626 A1 | 7/2005 | Karpf | |
| 2006/0184493 A1* | 8/2006 | Shiffman et al. | 706/47 |
| 2007/0250429 A1* | 10/2007 | Walser et al. | 705/37 |
| 2008/0052259 A1 | 2/2008 | Shiffman et al. | |
| 2011/0082827 A1 | 4/2011 | Shiffman et al. | |

FOREIGN PATENT DOCUMENTS

| | | |
|---|---|---|
| FR | 2686497 A1 | 7/1993 |
| WO | WO 88/02237 A1 | 4/1988 |
| WO | WO 89/05116 A1 | 6/1989 |
| WO | WO 94/01040 A1 | 1/1994 |
| WO | WO 94/01049 A1 | 1/1994 |
| WO | WO 94/13198 A1 | 6/1994 |
| WO | WO 94/24929 A1 | 11/1994 |
| WO | WO 96/13790 A1 | 5/1996 |
| WO | WO 98/38909 A1 | 9/1998 |
| WO | WO 99/27483 A1 | 6/1999 |
| WO | WO 99/38052 A1 | 7/1999 |
| WO | WO 00/75748 A2 | 12/2000 |
| WO | WO 00/15103 A1 | 1/2001 |
| WO | WO 01/06433 A1 | 1/2001 |
| WO | WO 01/09701 A1 | 2/2001 |
| WO | WO 00/75748 A3 | 4/2001 |
| WO | WO 01/26020 A1 | 4/2001 |
| WO | WO 01/26021 A1 | 4/2001 |
| WO | WO 01/34024 A1 | 5/2001 |
| WO | WO 01/74229 A2 | 10/2001 |
| WO | WO 02/19247 A2 | 3/2002 |
| WO | WO 01/74229 A3 | 5/2002 |
| WO | WO 02/19247 A3 | 11/2003 |
| WO | WO 2006/009331 A1 | 1/2006 |

OTHER PUBLICATIONS

U.S. Appl. No. 13/211,133, filed Aug. 16, 2011, Hufford et al.

Office action dated Oct. 14, 2011 for U.S. Appl. No. 12/965,719.

Final office action mailed Apr. 29, 2010 in connection with U.S. Appl. No. 09/825,533.

Final office action mailed Sep. 8, 2006 in connection with U.S. Appl. No. 09/825,533.

Non-final office action mailed Apr. 3, 2009 in connection with U.S. Appl. No. 09/825,533.

Non-final office action mailed Feb. 9, 2006 in connection with U.S. Appl. No. 09/825,533.

Non-final office action mailed Feb. 19, 2010 in connection with U.S. Appl. No. 11/844,632.

Non-final office action mailed May 20, 2008 in connection with U.S. Appl. No. 09/825,533.

Final office action dated Nov. 26, 2010 for U.S. Appl. No. 09/825,533.

Kamarck, et al. The Diary of Ambulatory Behavioral States: A new Approach to the Assessment of Psychosocial Influences on Ambulatory Cardiovascular Activity. Technology and Methods in Behavioral Medicine (D.S. Krantz and A. Baum, eds.) Lawrence Erlbaum Associates:Mahwah, New Jersey. 1998; Chapter 9:163-193.

Lussier et al. PureMD: a Computerize Patient Record Software for Direct Data Entry by Physicians: Using a Keyboardless Pen-Based Portable Computer. American Medical Informatics Association, McGraw Hill. 1992;261-264.

Bradburn, et al. Answering autobiographical questions: the impact of memory and inference on surveys, Science. Apr. 10, 1987;236(4798):157-161.

Collins, et al. Ecological momentary assessment in a behavioral drinking moderation training program. Exp. Clin. Psychopharmacol. Aug. 1998;6(3):306-315.

Cramer, et al. How often is medication taken as prescribed? JAMA Jun. 9, 1989;261(22):3273-3277.

Dahlstrom et al. Patient Computers to Enhance Compliance with Completing Questionnaires: a Challenge for the 1990s. Patient Compliance in Medical Practice and Clinical Trials (ed. By J.A. Cramer and B. Spilker). New York: Raven Press;1991: 233-40.

Eich, et al. Memory for Pain: Relation between Past and Present Pain Intensity. Pain 1985;23:375-380.

Engfer, et al. Technology in service of science. Invivodata, Inc. Jan. 30, 2001 (9 pages).

Friedman, W Memory for the Time of Past Events. Psychological Bulletin 1993; 113(1):44-66.

Gorin et al. Recall Biases and Cognitive Errors in Retrospective Self-Reports: A Call for Momentary Assessments. Handbook of Heath Psychology. Lawrence Erlbaum Assoc.:Mahwah, New Jersey. 2001;pp. 405-413.

Greeno, et al. Binge antecedents in obese women with and without binge eating disorder. J. Consult Clin. Psychol. Feb. 2000;68(1):95-102.

Hufford, et al. Collecting reliable and valid real-time patient experience data. Drug Information Journal. 2001; 755-765.

Hufford, et al. Correspondence between paper and electronic visual analog scales among adult asthmatics. Invivodata. Nov. 9, 2001.

Hufford, et al. Quality of life and patient experience research. Invivodata, Inc. Jan. 30, 2001 (10 pages).

Hyland, et al. Diary keeping in asthma: comparison of written and electronic methods. BMJ Feb. 20, 1993;306(6876):487489.

Invivodata Announcement dated Jun. 13, 2000.

Invivodata company newsletter dated 4th quarter 2001.

Invivodata company press release dated Apr. 11, 2001: Invivodata leads way in clinical trial technology with wireless patient diary system.

Invivodata company press release dated Jun. 12, 2000: Invivodata delivers new version of patient compliance monitoring.

Invivodata company press release dated Jun. 12, 2000: Invivodata Inc. provides science-based system to measure patient experience.

Invivodata company press release dated Nov. 28, 2000: Invivodata is first to guarantee patient compliance in clinical studies.

Invivodata company press release dated Oct. 12, 2000: Invivodata and RxCCI announce new partnership to improve quality and timeliness of clinical trials.

Invivodata postcard mail item. 2001.

Invivodata, Inc. Insights. Third Issue. Jul. 2001.

Invivodata. Application brief pain. Apr. 10, 2001 (2 pages).

Invivodata. Comparing electronic and paper diary data. Invivodata. Nov. 26, 2001.

Invivodata. Guaranteed patient compliance. Insight into patient behavior. Reduced study risks. Jul. 2001.

Invivodata. Innovations in Clinical Trial Technologies. Schedule for Seminar. 2001.

Invivodata. Prove it—your drug's performance beats the competition. Date?.

Kamarck, et al. Effects of task strain, social conflict, and emotional activation on ambulatory cardiovascular activity: daily life consequences of recurring stress in a multiethnic adult sample. Health Psychol. Jan. 17, 1998;(1): 17-29.

Kamarck, et al. Emotional Support Moderates the Acute Pressor Effects of Stress During Daily Life Abstracts of Papers for 1999 Annual Meeting: Paper Session: Cardiovascular Activity in Relation to Stress Psychology and Neurobiology. Psychosomatic Medicine 1999;61(1):112 (abstract).

Kamarck, et al. The effects of psychosocial influences on ambulatory blood pressure: contrasting different measurement and data analytic strategies. 37th Annual Meeting of the Society for Psychophysical Research, N. Falmouth, Massachusetts; USA, Oct. 15-19, 1997; Psychophysiology 1997;34 (Suppl. 1):S6-S7.

Kiuchi et al. A World Wide Web-based User Interface for a Data Management System for Use in Multi-institutional clinical trials—Development and Experimental Operation of an Automated Patient Registration and Random Allocation System. Controlled Clinical Trials. New York: Elseviar Sciences, Inc.;1996:(17)476-493.

O'Connell, et al. Coping in real time: using Ecological Momentary Assessment techniques to assess coping with the urge to smoke. Res. Nurs. Health. Dec. 21, 1998;(6):487497.

O'Connell, et al. Overcoming the Urge to Smoke: The Strategies of Long-Term Abstainers and Later Relapsers. Psychology of Addictive Behavior 1991;5(1):1-8.

O'Connell, et al. Reversal theory and smoking: a state-based approach to ex-smokers' highly tempting situations. J. Consult. Clin. Psychol. Aug. 1990;58(4):489-494.

O'Connell, et al. Symptom beliefs and actual blood glucose in type II diabetes. Res. Nurs. Health. Jun. 13, 1990;(3): 145-151.

O'Connell, K Why rational people do irrational things. The theory of psychological reversals. J. Psychosoc. Nurs. Ment. Health Serv. Jan. 29, 1991;(1):11-14.

Patrick, et al. Patient-reported outcomes to support medical product labeling claims: FDA perspective. Value in Health. 2007; 10, S125-S137.

Paty, et al. The importance of assessing base rates for clinical studies: an example of stimulus control of smoking. The Experience of Psychopathology: Investigating Mental Disorders in their Natural Settings (DeVries, Marten W. ed.) Cambridge University Press:Cambride, England. 1992; pp. 347-352.

Penner, et al. Individual Differences in Intraperson Variability in Mood. Journal of Personality and Social Psychology 1994;66(4):712-721.

Potocky, et al. State-outcome consistency in smoking relapse crises: a reversal theory approach. J. Consult. Clin. Psychol. Apr. 1991;59(2):351-353.

Powell, J. Handhelds aid doctors. Retrieved from the Internet, www.bostonherald.com/business/technology/ palm07032000.htm. Jul. 3, 2000.

Raynor, et al. The effects of social influence on cardiovascular responsiveness in the natural environment. 37th Annual Meeting of the Society for Psychophysical Research, N. Falmouth, Massachusetts, USA, Oct. 15-19, 1997. Psychophysiology 1997;34 (Suppl. 1):S73.

Ross, M Relation of Implicit Theories to the Construction of Personal Histories Psychological Review 1989;96(2):341-357.

Salford Systems. CART® for Windows User's Guide. A Salford Systems Implementation of the Original CART Program. 1999;i-v, 1-90, Index.

Schwartz, et al. Does trait coping exist? A momentary assessment approach to the evaluation of traits. J. Pers. Soc. Psychol. Aug. 1999;77(2):360-369.

Schwartz, et al. Strategies for analyzing ecological momentary assessment data. Health Psychol. Jan. 1998;17(1):6-16.

Shiffman, et al. A day at a time: predicting smoking lapse from daily urge. J. Abnorm. Psychol. Feb. 1997;106(1):104-116.

Shiffman, et al. Comparative efficacy of 24-hour and 16-hour transdermal nicotine patches for relief of morning craving. Addiction Aug. 2000;95(8): 1185-1195.

Shiffman, et al. Drinking and Smoking: A Field Study of their Association. Annals of Behavioral Medicine 1994;16(3):203-209.

Shiffman, et al. Dynamic effects of self-efficacy on smoking lapse and relapse Health Psychol. Jul. 2000;19(4):315-323.

Shiffman, et al. First lapses to smoking: within-subjects analysis of real-time reports. J. Consult. Clin. Psychol. Apr. 1996;64(2):366-379.

Shiffman, et al. Individual differences in the context of smoking lapse episodes. Addict. Behav. Nov.-Dec. 1997;22(6):797-811.

Shiffman, et al. Methods of measuring patient experience: Paper versus electronic patient diaries. Invivodata, Inc. Jan. 30, 2001 (9 pages).

Shiffman, et al. Nicotine withdrawal in chippers and regular smokers: subjective and cognitive effects. Health Psychol. Jul. 1995;14(4):301-309.

Shiffman, et al. Patient experience: A growing focus in clinical trials. Invivodata, Inc. Jan. 30, 2001 (8 pages).

Shiffman, et al. Progression from a smoking lapse to relapse: prediction from abstinence violation effects, nicotine dependence, and lapse characteristics. J. Consult. Clin. Psychol. Oct. 1996;64(5):993-1002.

Shiffman, et al. Remember that? A comparison of real-time versus retrospective recall of smoking lapses. J. Consult. Clin. Psychol. Apr. 1997;65(2):292-300.

Shiffman, et al. Subject experience diaries in clinical research, Part 1: The patient experience movement; Part 2: Ecological momentary assessment. Applied Clinical Trials. Feb. & Mar. 2001 (12 pages).

Shiffman, et al. Temptations to smoke after quitting: a comparison of lapsers and maintainers. Health Psychol. Nov. 1996;15(6):455-461.

Shiffman, et al. The Abstinence Violation Effect Following Smoking Lapses and Temptations. Cognitive Therapy and Research 1997;21(5):497-523.

Shiffman, et al. The effect of bupropion on nicotine craving and withdrawal. Psychopharmacology Jan. 2000;148(1):33-40.

Shiffman, et al. The scientific principles underlying patient experience research: Ecological momentary assessment. Invivodata, Inc. Jan. 30, 2001 (8 pages).

Shiffman, S. Assessing Smoking Patterns and Motives. Journal of Consulting and Clinical Psychology 1993;61(5):732-742.

Shiffman, S. Real-Time Self-Report of Momentary States in the Natural Environment: Computerized Ecological Momentary Assessment. The Science of Self-Report: Implicates for Research and Practice (A. Stone, et al. eds.) Lawrence Erlbaum Associates:Mahwah, New Jersey, 1989; Chapter 16: 277-296.

Smith, G. Statistical Reasoning 3rd edition. Needham Heights: Allyn and Bacon; 1991:619-67.

Stone, et al. A comparison of coping assessed by ecological momentary assessment and retrospective recall. J. Pers. Soc. Psychol. Jun. 1998;74(6):1670-1680.

Stone, et al. Does the peak-end phenomenon observed in laboratory pain studies apply to real-world pain in rheumatoid arthritics? The Journal of Pain. Fall 2000;1(3):212-217.

Stone, et al. Ecological Momentary Assessment (EMA) in Behavioral Medicine. Annals of Behavioral Medicine 1994; 16(3): 199-202.

Stone, et al. Ecological Momentary Assessment. Well-being: The foundations of Hedonic psychology. Kahneman, Daniel et al. (eds.). Russell Sage Foundation: New York, NY. 1999;pp. 26-39.

Straka, et al. Patient and self-reporting of compliance does not correspond with electronic monitoring: an evaluation using isosorbide dinitrate as a model drug. Pharmacotherapy. Jan.-Feb. 1997.;17(1):126-132.

Tattersall et al. The Use of a Hand-held Computer to Record Clinical Trial Data in General Practice: a Pilot Study. The Journal of International Medical Research. 1989;17:185-89.

Taylor et al. The use of a real-time computer diary for data acquisition and processing. Behav. Res. Ther.1990;(28)1:93-97.

Tomkies, K. Taking a New Tack on Clinical Trial Data Collection: New Internet-based software aims to improve data integrity, helping speed data transmission in the process. Retrieved from the Internet www.office.com/global/0,,53-17789,FF.html. May 18, 2000.

Totterdell et al. In situ repeated measures of affect and cognitive performance facilitated by use of a hand-held computer. Behavior Research Methods, Instruments and Computers. 1992;24(4):545-53.

Weisspeiner, et al. Multichannel Ambulatory Monitoring of Circulation Related Biosignals. Proceedings. Computers in Cardiology, Sep. 23-26, 1991; Venice, Italy. IEEE Comput. Soc. Press: Los Alamitos, CA, USA. 1991;p. 457-460.

Zimmet et al. Computer-Based Patient Monitoring Systems: Use in Research and Clinical Practice. Diabetes Care. Nov./Dec. 1988; (11) Supp. 1:62-6.

Mitchel, et al. The impact of electronic data capture on clinical data management: perspectives from the present into the future. Technology in Clinical Research. Aug. 2008; 37-41.

U.S. Appl. No. 13/399,150, filed Feb. 17, 2012, Hufford et al.

Office action dated Mar. 13, 2012 for U.S. Appl. No. 12/965,719.

Alwan, et al. A Smart and Passive Floor-Vibration Based Fall Detector for Elderly. Information and Communication Technologies, 2006. ICTTA '06. 2nd vol. 1, Apr. 24-28, 2006 pp. 1003-1007.

Lorence, et al. Incremental adoption of information security in health-care organizations: implications for document management. IEEE Trans Inf Technol Biomed. Jun. 2005;9(2):169-73.

Notice of allowance dated Jun. 3, 2008 for U.S. Appl. No. 11/324,504.

Notice of allowance dated Sep. 24, 2004 for U.S. Appl. No. 09/825,534.

Office action dated Nov. 14, 2007 for U.S. Appl. No. 11/324,504.

Park, et al. 3B-1 Noninvasive Insulin Delivery in Large Pigs (> 100 lbs) Using the Lightweight Cymbal Array. Ultrasonics Symposium, 2007. IEEE Oct. 28-31, 2007 pp. 104-107 Digital Object Identifier 10.1109/ULTSYM.2007.39.

Shalev, et al. Towards an expert system for treatment planning. Engineering in Medicine and Biology Society, 1988. Proceedings of the Annual International Conference of the IEEE Nov. 4-7, 1988 pp. 1444-1445, vol. 3 Digital Object Identifier 10.1109/IEMBS.1988. 95302.

Shiffman, et al. Introduction to the special section: Ecological momentary assessment in health psychology. Health Psychology. Jan 1988; 17(1):3-5.

Office action dated Oct. 11, 2012 for U.S. Appl. No. 12/965,719.

* cited by examiner

CLINICAL TRIAL ENDPOINT DEVELOPMENT PROCESS

CROSS-REFERENCE

This application claims the benefit of U.S. provisional application No. 61/083,575, filed Jul. 25, 2008, which is incorporated herein by reference in its entirety.

BACKGROUND OF THE INVENTION

A clinical trial is a study following a pre-designed protocol to consider the effectiveness of a treatment for biomedical or health-related benefit in humans. Most clinical trials are either interventional or observational types of studies. In interventional studies, an investigator measures an outcome of an intervention, usually in the form of a treatment given to a group of subjects. In observational studies, an investigator would record what he or she observes from the subjects subjected to a study protocol.

In general, there are five different types of trials. Treatment trials test for the effectiveness of experimental treatments, such as new combinations of drugs, or new approaches to surgical or radiological method. On the other hand, prevention trials attempt to find better ways to prevent disease in people who have not experienced the disease. Another focus of a prevention trial is to prevent the disease from returning in subjects experienced with the disease. An exemplary approach is a vaccine trial. Prevention trials can use medicines, vitamins, minerals, or lifestyle changes. Diagnostic trials are studies designed to find more convenient, accurate, easily accessible, and rapid procedures for the diagnosis of a disease or condition. Screening trials focus on better ways to aid earlier and accurate detection of a disease or a health conditions. Lastly, quality of life trials, also called supportive care trials, inquire into ways to improve comfort and the quality of life for subject with a chronic disease.

A clinical protocol is a pre-designed, written guideline detailing the type, objective, and requirements (such as devices, supportive infrastructure, and subject characteristics) of a clinical trial, and the clinical trial endpoints. A clinical trial endpoint can include a state of a disease, a symptom, or a clinical sign which mirrors the target goal of a trial. In a typical setting, what are actually measured in a clinical trial are clinical trial endpoints. Combined results obtained from a variety of measured clinical trial endpoints are often evaluated in terms of their support of one or more clinical objectives or goals. The use of clinical trial endpoints such as tumor size, physiological data, vital signs associated with a state of healthiness or expression of well-being enable an investigator to quantitatively measure the effectiveness of a medical product to the stated goal of a trial. For example, chest pain can be used as a clinical trial endpoint in a clinical trial investigating the ability of a medical product to prevent a heart attack. When a subject is enrolled in the clinical trial and a medical product over a period of time, the subject can report back to an investigator any episodes of chest pain over the course of the trial. The number of subjects reporting chest pain and/or the number of incidences of chest pain in each subject can be quantified and expressed as a fraction to the entire population of subjects enrolled in the clinical trial. In some examples a medical product is administered to a first group of subjects and a placebo is administered to a second group of subjects. The results observed in the group of subjects administered a medical product can be compared to the results in the observed in the group of subjects administered a placebo- to determine if there is a causative relationship between the medical intervention and the clinical trial endpoint.

A surrogate endpoint is a measure of an effect of a certain treatment that can correlate with a clinical endpoint but does not necessarily have a guaranteed relationship. The National Institutes of Health defines a surrogate endpoint as a biomarker intended to substitute for a clinical endpoint. Surrogate markers are used when the primary endpoint is not desirable, such as death, or very difficult to attain and thus making it impractical to conduct a clinical trial to gather a statistically significant number of clinical endpoints. An example of a surrogate endpoint is the level of cholesterol in a clinical trial testing a medical product in a group of patients with cardiovascular disorder. While above normal cholesterol levels in a subject can increase the chances of a cardiovascular disorder, the relationship is not an absolute indicator of risk as some subjects with above normal levels of cholesterol do not develop cardiovascular disorder or show signs of heart disease.

Some clinical trial endpoints are qualitative and subjective indicators. In a clinical trial, subjective indications can be quantified by assigning numeric values to indicate the intensity of pain or experience. The measurement of a subjective indication is a difficult undertaking as it can be affected by subtle differences in the design of the clinical trial. For example, when a subject is posed the question "do you experience pain", the answer can be markedly affected by the manner in which the question is presented. For example, when a person is given a range of scores to choose in response to a question of severity of pain, the answer provided can be affected by environmental cues, such as whether or not the question is presented on a graphical display or is asked by a person. Responses can also be affected by variables such as the color or size of a screen display. The characteristics of the person, such as gender, age, friendliness, profession (trained interviewer, psychiatrist, clinician, health care administrator, etc); presenting the question can also affect the answers provided. Other variables that can affect an answer include the time of the question, the room environment (closed, open), or whether a multiple choice or a numeric scale is used by a subject to select an answer.

A clinical trial endpoint can reliably predict the clinical outcome of a subject. Under some conditions, satisfying the clinical trial endpoint indicates that a desired outcome has been successfully reached. Multiple clinical trial endpoints in a trial can be combined to corroborate an indication that a clinical trial goal is met by a medical product. Careful clinical trial design allows the use of subjective indications, to be employed in a clinical trial to validate the goal of the trial.

In the past, subjective indications in a clinical setting have generally been recorded by clinicians or caregivers. However, the experiences recited by a subject is filtered and rephrased by the person administering the interview. Recently, the filtering was recognized as one of the factors contributing to the potential unreliability of subjective indications as clinical endpoints. Therefore, modern clinical trials have begun to develop better ways to produce more comprehensive pictures of subjective indications such as the status of a subject in terms of their symptoms and the impact of those symptoms on the subject's daily life.

Patient-reported outcome (PRO) is a measurement of an aspect of a subject's health status that comes directly from the subject (i.e., without the interpretation of the subject's responses by a physician or anyone else). A PRO instrument can be used to obtain a measurement by questionnaire, diary, or other forms of media allowing verbal or written expression of health status. In one embodiment, a health-related quality of life (HRQOL) questionnaire is a PRO instrument and is used to evaluate physical, social, psychological functioning of a subject.

SUMMARY OF THE INVENTION

In one aspect of the invention a method is provided for clinical trial endpoint development comprising: administering one or more questions to a subject who is administered a medical product or a placebo, wherein said one or more questions are administered to said subject by a portable electronic device, wherein said device records data about said subject's response to said one or more questions ; analyzing said data; developing one or more clinical trial endpoints based on said analysis of said data; and, using said one or more clinical trial endpoints in a clinical trial as an indicator to determine when one or more goals of said clinical trial is reached. In one embodiment the step of administering a questionnaire to a subject is part of a pilot trial. In another embodiment analyzing said data is performed on said portable electronic device. In another embodiment analyzing said data comprises sending said data to a data analysis system, wherein said data is analyzed. In another embodiment the clinical trial tests a medical product or a placebo on a human subject. In another embodiment, the developing comprises modifying said questionnaire based on said evaluation of data and repeating the first and second steps. In another embodiment, the analyzing comprises psychometric validation of said data. In another embodiment the one or more questions comprises at least one a health-related quality of life (HRQOL) question. In another embodiment, the administering comprises prompting said subject to answer said one or more questions. In another embodiment, the prompting lasts for the duration of said clinical trial. In another embodiment, the wherein prompting occurs at a pre-scheduled time or a random time. In another embodiment the data is sent to the data analysis system by a wireless connection or wired connection. In another embodiment the data comprises information on the time said subject responds to said one ore more questions, the date said subject responds to said one ore more questions, or the location of said portable electronic device when said subject responds to said one ore more questions. In another embodiment one of said one or more goals of said clinical trial is to assess a label claim of a medical product. In another embodiment the second step comprises analyzing said data for one or more evaluative indicators. In another embodiment analyzing comprises a statistical hypothesis test of said evaluative indicators. In another embodiment the statistical hypothesis test is a t-test or a probability value test. In another embodiment the data comprises patient-reported outcome (PRO) data or metadata.

In another aspect of the invention a method is provided for developing a questionnaire for use in a clinical trial comprising: administering one or more questions to a subject who is administered a medical product or a placebo and recording said subject's response to said one or more questions as a first set of data; analyzing said first set of data to determine the validity or reliability of said question; accepting said question for collection in step e), or modifying said question and providing it again in the first step; collecting said one or more questions into a questionnaire; administering said questionnaire to a subject in a clinical trial, wherein said administering is by a portable electronic device, wherein said portable electronic device records said subject in a clinical trial's response as a second set of data; analyzing said second set of data to determine if a predetermined clinical trial endpoint has been reached in said clinical trial. In one embodiment, the questionnaire comprises one or more HRQOL questions. In another embodiment, the analyzing step comprises analyzing said data for one or more evaluative indicators. In another embodiment, the first or second set of data comprises PRO data or metadata.

In another aspect of the invention a computer program product is provided comprising a computer readable medium having computer program logic encoded thereon for enabling a processor to develop a clinical trial endpoint comprising: a receiving procedure that enables a processor to receive data from a portable electronic device, wherein said data comprises a response to one or more questions responded to by a subject who was administered a medical product or a placebo, wherein said one or more questions are administered to said subject by said portable electronic device; an analyzing procedure to analyze said data; an output procedure to provide one or more clinical trial endpoints based on said analysis of said data. In one embodiment, the analyzing step comprises analyzing said data for one or more evaluative indicators. In another embodiment, the computer program product of claim 23, wherein said data comprises PRO data or metadata.

In another aspect of the invention a computer system for clinical trial endpoint development is provided, comprising a computer readable medium having computer program logic encoded thereon, wherein said computer program logic comprises instructions, which comprise: input instructions for receiving data from a portable electronic device, wherein said data comprises a response to one or more questions responded to by a subject who was administered a medical product or a placebo, wherein said one or more questions are administered to said subject by said portable electronic device; analysis instructions for analyzing said data; output instructions for providing one or more clinical trial endpoints based on said analysis of said data. In one embodiment, the analyzing step comprises analyzing said data for one or more evaluative indicators. In one another embodiment, the data comprises PRO data or metadata. In another embodiment, the computer system further comprises instructions to send information to said portable electronic device, wherein said computer system is remote from said portable electronic device. In one embodiment, the information comprises one or more questions.

In another aspect of the invention a computer program product is provided comprising a computer readable medium having computer program logic encoded thereon for enabling a processor to develop a questionnaire for use in a clinical trial comprising: a receiving procedure that enables a processor to receive data from a portable electronic device, wherein said data comprises a response to one or more questions responded to by a subject who was administered a medical product or a placebo; an analyzing procedure to analyze said data to determine the validity or reliability of said question, wherein said procedure collects a question determined to be valid or reliable and outputs them for use in a clinical trial questionnaire or said procedure modifies a question determined to be invalid or unreliable and outputs them for administration to a subject who is administered a medical product or a placebo; an output procedure to provide a validated or reliable question for use in a clinical trial or to provide a modified question to a subject who is administered a medical product or a placebo. In one embodiment the analyzing step comprises analyzing said data for one or more evaluative indicators. In another embodiment, the data comprises PRO data or metadata.

In another aspect of the invention a computer system is provided for providing a questionnaire for use in a clinical trial comprising a computer readable medium having computer program logic encoded thereon, wherein said computer program logic comprises instructions, which comprise: input instructions for receiving data from a portable electronic device, wherein said data comprises a response to one or more questions responded to by a subject who is administered a medical product or a placebo; analysis instructions for analyzing data to determine the validity or reliability of said question, wherein said procedure collects a question determined to be valid or reliable and outputs them for use in a clinical trial questionnaire or said procedure modifies a question determined to be invalid or unreliable and outputs them for administration to a subject who is administered a medical product or a placebo; output instructions to provide a validated or reliable question for use in a clinical trial or to provide a modified question to a subject who is administered a medical product or a placebo. In one embodiment, the data comprises PRO data or metadata.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
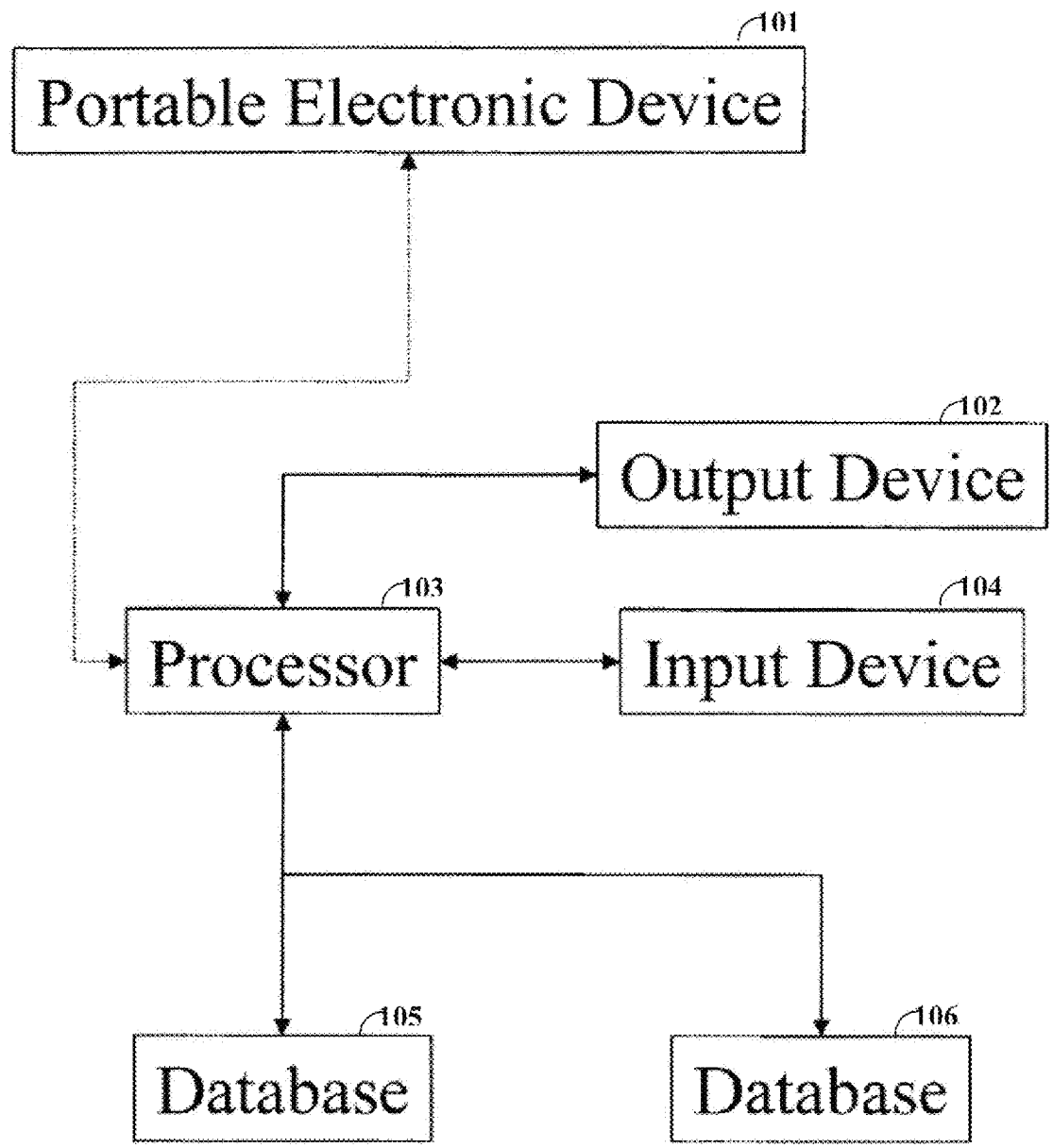
FIG. 1 illustrates a system for developing a PRO-data based clinical trial endpoint.
Figure 2:
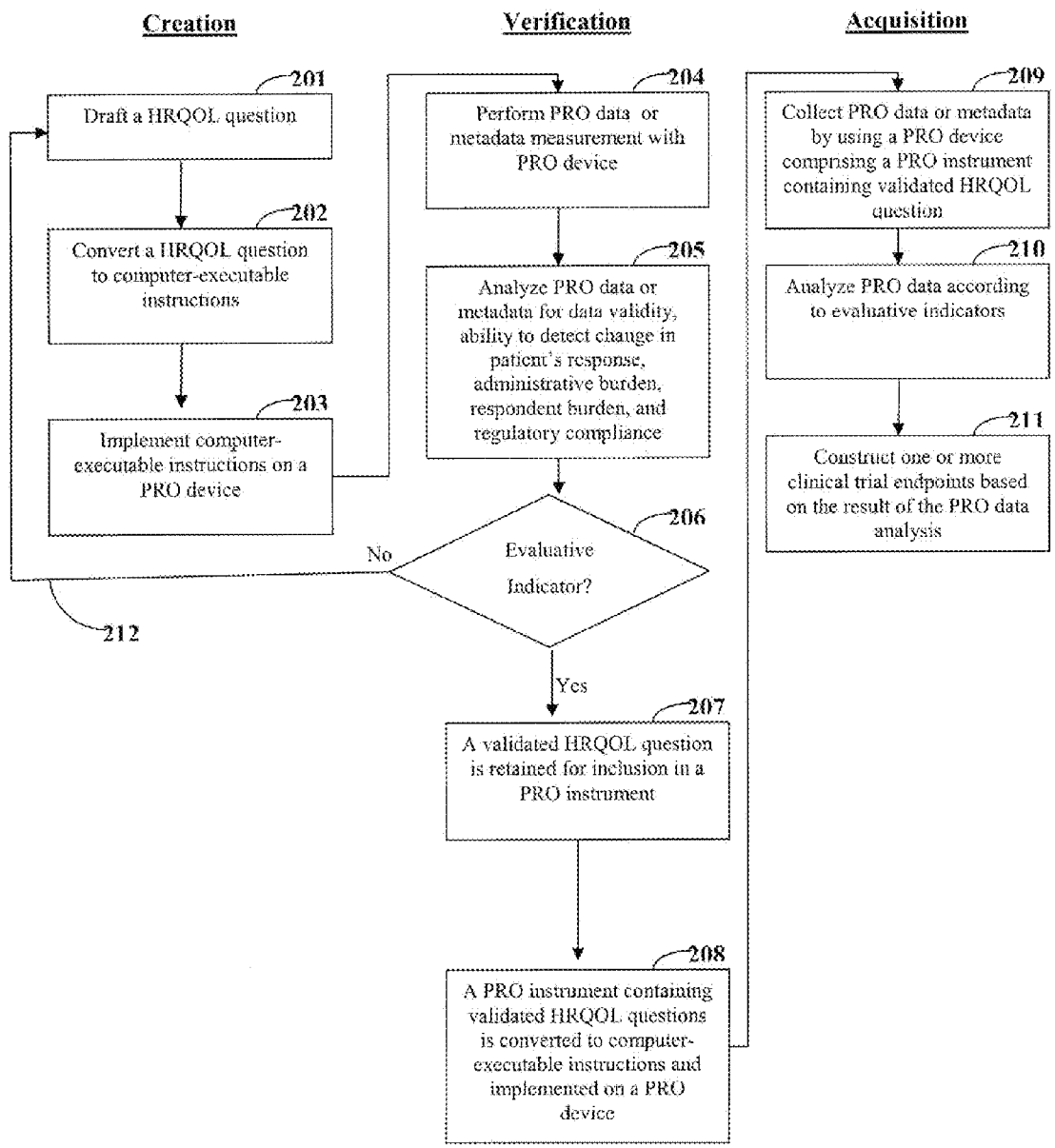
FIG. 2 illustrates one embodiment of designing HQRL question for a use in a clinical trial employing PRO-data collection for constructing a clinical trial endpoint.

One aspect of the invention is directed to devices and methods for assessing patient reported outcome (PRO) data from a portable electronic device to support a label claim for a medical product. Generally, such a label claim must be approved by a regulatory agency, such as the United States Food and Drug Administration (FDA) or evaluated by a scientific agency, such as the European Medicines Agency (EMA). In this context, a label claim can be a statement of a health benefit of a medical product or comparative safety advantage. Normally, evidence or data must be submitted to the FDA to support a label claim. Often, a clinical trial is designed to test and collect evidence in support of a label claim that is made for a medical product. PRO data can be collected and used to support medical labeling claims. In one embodiment, a clinical trial endpoint based on PRO data validated by the methods disclosed herein can be used in support of medical product label claims.

Definitions

A "clinical endpoint" as used herein, refers to occurrence of, or change in, a disease, a condition, a syndrome, a symptom, a sign or a laboratory measurement in a subject that constitutes one of the target outcomes of a clinical trial.

A "clinical trial" as used herein, refers to an experimental trial or test on one or more subjects designed to determine the safety, efficacy, or basis of a label claim for a medical product. A clinical trial includes administering a medical product or a placebo to one or more subjects.

A "clinical trial endpoint" as used herein, includes both a clinical endpoint and a surrogate endpoint.

An "evaluative indicator" as used herein, includes measurements of the reliability or validity of the PRO data. Reliability can be specified as internal consistency, test-retest, and parallel forms reliability. Reliability can be expressed as a reliability coefficient, such as but not limited to, Cronbach's alpha, intra-class correlation, or Pearson and Spearman correlation. Validity can be specified as content and criterion-related or construct validity. Validity can be expressed as a validity coefficient, such as, but not limited to a Pearson correlation coefficient. Sensitivity and responsiveness to change estimates can also be validity coefficients. They can be expressed as an effect size or another estimate known in that arts that characterizes the extent to which scores produced by a PRO instrument change when the underlying concept also changes, or in response to an effective treatment.

A "computer-executable instruction" as used herein, refers to an instruction or a set of instructions able to operate a computer processor to achieve a desired functional result. The desired functional result can be simple, such as the storage of a value in memory, or complex, such as an invocation of an advanced programming interface (API) call that produces sophisticated functionality. The instruction set can be any suitable processor-executable instruction set, including (without limitation) a native machine architecture language, machine language, Java, JavaScript, BASIC, Visual BASIC, C, C++, C#, FORTRAN, Perl, a command shell scripting language. etc. The instruction set can be declarative, such as HTML or XTML; imperative, such as C; a hybrid language; another type of instruction set; etc. The instruction set can be fully compiled, such as into a machine-executable binary; partially compiled into an intermediate language that is subsequently fully compiled; interpreted from text, etc. The instruction can be executed natively on a processor; through a parser, advanced programming interface (API), or in a virtual machine; within another application or process, such as a web browser; etc. Any instruction can be used as long as the instruction is able to operate a computer to achieve the desired functional result.

A "label claim" as used herein, is a claim made regarding a medical product that is subject to regulatory approval by a government agency (such as the FDA) or evaluation by a government agency (such as the EMA), and includes, but is not limited to, an efficacy claim, a safety claim, a toxicity claim, a treatment claim, a health claim, a nutritional claim or a structure/function claim. A "label claim" can appear in any section of a medical product's packaging, advertising or other literature associated with the medical product.

A "medical product" as used herein, includes, but is not limited to, a drug, a biologic, a medical device (including surgical intervention), a dietary supplement or a cosmetic that is intended to have a human or veterinary use. A medical product includes a product intended to treat or prevent a disease, condition, syndrome or symptom. A medical product also includes a product intended to treat a sick, injured, or wounded human or non-human animal. A medical product also includes a product intended to improve a subject's health, wellbeing, state of mind or appearance. A medical product includes a pharmacologically active compound, an implantable device and a surgical procedure.

"Metadata" as used herein, refers to data about PRO data or a subject's use of a PRO device. Metadata can include information on when (time or date) a subject completed a question, the amount of time a subject took to complete a question, the length of a delay before responding to a prompt to answer a question, the length of time between answering questions the number of times a subject changed an answer for a question, the content of a preliminary answer to a question where the answer was later changed, the physical location of the PRO device when a subject answered a question.

A "patient" as used herein, is a human individual with a disease, condition, syndrome or symptom, or who is sick, injured, or wounded.

A "placebo" as used herein, is a substance, device or procedure that is objectively without specific activity for the disease, condition, syndrome or symptom being treated. A placebo includes a compound that is pharmacologically inert or a sham surgical procedure.

A "PRO device" as used herein, is a device which is used to administer a PRO instrument to a subject to acquire PRO data or metadata. A PRO device can be a portable electronic device or a fixed electronic device such as a desktop computer or work station terminal.

A "PRO instrument" as used herein, comprises a questionnaire, diary, or other form of media that can be used to obtain verbal, written, typed or tactile PRO data from a subject. A PRO instrument can be a health-related quality of life (HRQOL) questionnaire. A PRO instrument can be used to evaluate the physical, social, or psychological state of a subject. A PRO instrument can be designed to include one or more questions that have been vetted to optimize the form (e.g., graphical; textual or a combination thereof), phrasing or timing of the question to a subject in order to acquire PRO data that is more likely to be valid as compared to data acquired from a non-vetted question. A PRO instrument can be encoded as a computer-executable instruction to be performed on a PRO device.

"PRO data" as used herein, is patient reported outcome data that is acquired from a subject who is or was a participant in a clinical trial of a medical product. The PRO data can be obtained directly from the subject or from a subject's surrogate (such as in instances where a subject is unable to directly provide some or all of the data). PRO data includes a spontaneous expression by a subject about his or her health, well being, psychological state, appearance, or functionality, or a response to a query to a subject about his or her health, well being, psychological state, appearance, or functionality. PRO data includes information such as PRO concepts.

A "portable electronic device" used herein refers to any electronic device that can be adapted for use by a subject and/or clinical staff for viewing and/or inputting information. Preferably, the portable electronic device will also have a visual, audible or tactile alarm to gain the attention of a subject. For example, a pager, cell phone or a personal digital assistant (PDA) having a vibration alarm can be used as a portable electronic device. Further examples include but are not limited to: a pager, a cell phone (including a smart phone) or a PDA with audible alarms or text messaging capabilities, a laptop computer, or a net book computer. A portable electronic device can be a handheld computational device provided with a display, a data input feature (such as a touch-sensitive screen or buttons, e.g. a keyboard) to enable a subject to respond to a question posed on the display or speaker, or to input unsolicited information. Examples of such portable electronic devices include, but are not limited to, a Blackberry by Research in Motion Ltd., a Palm Pilot by Palm, Inc or a Windows-based device running an operating system from Microsoft Corporation. The portable electronic device can be adapted to communicate with at least one other computer via a wired connection or a wireless connection, including the use of WiFi, a cellular network, a modem or a network (such as a local area network) or the Internet.

A "subject" as used herein, includes a patient that can be treated or diagnosed with a medical product. The term "subject" includes a human individual who is free of a disease, condition, syndrome or symptom and is being administered a prophylactic medical product in order to prevent the occurrence of the disease, condition, syndrome or symptom. The term "subject" includes a human individual who is being administered a medical product in order to benefit the individual's, health, wellbeing, state of mind or appearance.

A "surrogate endpoint" as used herein, is a measure of an effect of a medical product in a clinical trial on a human or non-human subject that correlates with a real clinical endpoint. The surrogate endpoint can be the presence, absence or change in the level of a biomarker.

In one embodiment, a method is provided is provided for analyzing patient reported outcome (PRO) data for compliance with FDA-approved guidelines for a clinical trial. In another embodiment, a method is provided is provided for analyzing patient reported outcome (PRO) data obtained from a subject in a clinical trial to determine if one or more clinical trial endpoints has been reached. In one embodiment the clinical trial is designed to test a medical product's label claim. In one embodiment when the one or more clinical trial endpoints is reached, it is used to substantiate a medical product label claim.

In one embodiment, a computer (e.g., a portable electronic device, a server, computer workstation or a desktop computer) comprising a processor-executable instruction is provided for analysis of PRO data or metadata to determine compliance with FDA-approved guidelines for a clinical trial. In another embodiment, a computer (e.g., a portable electronic device, a server or a desktop computer) comprising a processor-executable instruction for analysis of PRO data or metadata to design one or more clinical trial endpoints. In one embodiment the clinical trial endpoint is designed to substantiate a medical product's label claim. A clinical trial can be designed to obtain data related to one or more specific clinical trial endpoints. Clinical trial endpoints that are based on PRO data can be influenced by the clinical settings in which PRO data or metadata are collected. In one embodiment, a clinical trial endpoint is identified that serves as a valid indicator of the outcome of a clinical trial by taking into consideration the clinical setting. A clinical setting can influence a clinical trial endpoint. In one embodiment, a clinical trial is designed so that the assessment of PRO data-based clinical trial endpoints is minimally influenced by the clinical setting in which the clinical trial occurs. This can provide for better PRO data to be used to support one or more medical label claims.

In one embodiment, a clinical trial is completed when a specific clinical trial goal is met. In another embodiment a clinical trial results can show support for a medical product's label claim by meeting a specific clinical trial goal or clinical measurement. These clinical trial goals are also known as "concepts" (i.e., the characteristic or outcome) that is to be met. In one embodiment a clinical trial ends when a statistically significant number of subjects reach a clinical goal. In another embodiment a clinical trial has multiple phase with one or more goals for each phase. A phase ends when a statistically significant number of subjects reach a clinical goal, however the larger multi-phase clinical trial can continue.

In one embodiment a label claim can be substantiated when all concepts determined to be relevant for the label claim are articulated and supported by evidence obtained during the clinical trial (such as PRO data or metadata). Furthermore, concepts can be comprised of one or more domains.

A "domain" is a component of a concept. A domain can address a specific aspect of a label claim. A physical domain addresses matters of physical nature. An emotional domain addresses matters of emotional nature. Other examples are psychological, physiological, behavioral, or social domains. Some concepts are single-domain concepts. Most concepts addressing a symptom are single-domain concepts. Other concepts, such as health-related quality of life concepts, are multi-domain concepts. In one embodiment, a multi-domain concept can be satisfied by answering questions of a physiological domain, such as objective indicia of metabolic change or measurable change of a tumor size, but also answering questions of an emotional domain such as "are you feeling better than before the treatment was started?".

A clinical trial endpoint can be an enunciation of a concept. In one embodiment, if a concept is defined as pain relief, a clinical trial endpoint articulates the concept in a measurable term by employing a scale or a range to describe what is considered as relief of pain. For example, when pain relief is defined as a number 5 on a 0 to 10 scale (where 0 equals no pain and 10 is intolerable pain), a subject who is scoring 5 or who provides PRO data indicating his or her pain level is at a 5, can be considered as evidence the clinical trial endpoint has been achieved.

In one embodiment, a method is provided for developing PRO-data based clinical trial endpoints that exhibit statistically significant correlative power to the goal of a clinical trial. A result is called statistically significant if it is unlikely to have occurred by chance. The significance level of a test is a traditional statistical hypothesis testing concept. It can be defined as the probability of making a decision to reject the null hypothesis when the null hypothesis is actually true (a decision known as a Type I error, or "false positive determination"). The decision is often made using the p-value: if the p-value is less than the significance level, then the null hypothesis is rejected. The significance level is usually represented by the Greek symbol, $\alpha$ (alpha). In one embodiment the $\alpha$ level of significance is less than or equal to about 10%, such as about 9%, 8%, 6%, 5%, 4%, 3%, 2%, 1%, 0.1% or 0.001%. Smaller $\alpha$-levels give greater confidence in the determination of significance, but can run the risk of failing to reject a false null hypothesis (a Type II error, or "false negative determination"). If a test of significance provides a p-value lower than the $\alpha$-level, the null hypothesis is rejected. Such results are referred to as 'statistically significant'. The clinical trial endpoint development process comprises identifying requirements of a clinical trial, optionally consolidating PRO data or metadata, analyzing PRO data or metadata to determine whether the PRO data meets one or more evaluative indicators for trial objectives, developing a strategy for receiving the PRO data or metadata, either from a PRO device or from other forms of communication, and constructing a clinical trial endpoint based on the analysis of the PRO data. In one embodiment, the PRO device is a portable electronic device. The gathering, evaluating, and consolidating the PRO data can be accomplished by applying computer logic steps employing statistical algorithms for the treatment of data.

The identification step of clinical trial endpoint development can involve several phases. In one embodiment, during the first phase of the identification step, criteria for selection of a target population of a clinical trial are articulated, human subjects meeting the criteria are recruited, specific technical fields related to the clinical trial are listed, and technical experts familiar with the field are recruited. Afterward, to gather PRO data, a PRO instrument is created. In one embodiment the PRO instrument comprises a questionnaire that is drafted and optionally modified based on input from one or more experts. One example of such questionnaire is a heath-related quality of life (HRQOL) questionnaire.

The second phase of the identification step can involve gathering preliminary PRO data, which can include collecting reports from subjects involved in prior clinical trials, such as a first clinical trial. In one embodiment a first clinical trial is a pilot trial that enrolls a smaller number of subjects than the number of subjects in a second clinical trial. In one embodiment a pilot trial is designed to test the design of a PRO instrument, the design of one or more questions, or clinical trial design, with fewer subjects than in a subsequent clinical trial. In another embodiment, a first clinical trial enrolls a number of subjects greater than or equal to the number of subjects in a second clinical trial. In one embodiment, one or more pilot trials are performed and the PRO instrument is modified based on the analysis of the data from the pilot trial. In one embodiment, the modification comprises: an addition of a question to a questionnaire, a deletion of a question to a questionnaire, a change in the wording of a question in a questionnaire, a change in the format of a question in a questionnaire, or a change in the order of one or more questions in a questionnaire, a change in the time of day a question in a questionnaire is delivered, or a change in the prompting of a question in a questionnaire. In one embodiment, the question is a HRQOL question. In another embodiment, more than one pilot trial is performed in different clinical environments and the PRO questionnaire is modified based on the analysis of the more than one pilot trials. At this step, the modification can be focused on minimizing the influence from clinical settings. The modified questionnaire can be tested further to become more independent of environmental variables that can not be controllable under design of clinical study. In one embodiment data (such as PRO data or metadata) collected from a pilot trial is used to develop one or more clinical trial endpoints for a subsequent clinical trial.

In one embodiment, the pilot trial is of a shorter duration than a subsequent clinical trial. In another embodiment, the pilot trial has fewer clinical trial endpoints than a subsequent clinical trial. In another embodiment, the pilot trial enrolls fewer subjects than the subsequent clinical trial. In one embodiment, the pilot trial enrolls about 10% to 90% (such as about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 89%, or 90%) of the number of subjects of a subsequent clinical trial. In one embodiment, a pilot trial precedes a clinical trial and comprises administering the same medical product or medical products to one or more subjects as is administered in the clinical trial subsequent to the pilot trial.

The next phase of the identification step can include listing physical devices to be used in the clinical trial or customizing one or more devices for use in the clinical trial. In one embodiment, a PRO device is used in the clinical trial. A PRO device that interacts directly with a subject can be considered for modification in this step. For example, certain technical features of a PRO device can be too complex for a group of subjects. To avoid the possibility in which these features can discourage or hinder the subject from efficiently recording PRO data, customization of one or more PRO device or drafting instructional manuals attuned to the level of literacy of the intended population can be undertaken. Customization can include disabling or augmenting one or more of the physical features of a PRO device (such as a keyboard, display, communications ability or security measures) or modifying computer executable instructions on a PRO device (such as those encoding a PRO instrument). If a long period of time is required to record the data, or mobility of subjects is required, a device for accommodating longer time or subject mobility can be configured or designed.

Once the measurement system is selected, the manner of PROmeasurement is determined. Each PRO data entry is separately evaluated to determine whether a PRO entry is influenced by time, frequency, or location of measurements. For example, questions regarding feeling of nausea tend to give a falsely high score if measured in the morning. Questions regarding pain also have a tendency to give a falsely high score if measured at night. These known examples and other variables are considered by modifying time, frequency, or location of measurement and are tested further with various groups of subjects to provide a more reliable PRO measurement system.

In one embodiment, methods of assessing PRO data or metadata comprise evaluating each question in a questionnaire to determine if a random prompting method (e.g. prompting a subject with a query at a random time) is favorable over scheduled recordings of PRO data (e.g., prompting a subject with a query at a pre-determined time). In one embodiment, a random prompting method uses a PRO device (such as a portable electronic device) that prompts a subject to respond to a PRO question at a randomly given moment in time. If a random prompting is more favorable and seems to provide a more reliable method of measurements, consideration is given to the manner of random prompting, such as beeping, voice (male, female, child), music, vibration, or loudness of an audible prompt depending on the PRO device used. Scheduled prompting is based on a predetermined time schedule for prompting. A PRO device (e.g., a portable electronic device) capable of executing computer executable instructions can be employed to collect, store, consolidate, and analyze PRO data. Examples of such PRO devices which can be used with the methods of the present invention are disclosed in U.S. Pat. No. 6,879,970; and U.S. Patent Application Publication Nos: 2006/0184493; 2002/0143563; and 2002/0156640, which are herein incorporated by reference in their entirety.

In another embodiment, devices and methods of the invention comprise providing a questionnaire to a subject, and assessing one or more questions in the questionnaire to weigh the value of the answer given. Furthermore, the method can comprise assessment of the duration of each round of data entry. If it is unavoidable to have a long questionnaire with many questions, a PRO device. can be programmed to present one or a few questions at multiple time points. For example, if a given question shows increased variability in response when it is presented toward the end of a questionnaire as opposed to the beginning of a questionnaire, it can be desirable to shorten or break down the questionnaire. It can also be desirable to revalidate each question to determine whether or not different ways of administering the question has a significant effect on the variance of the answer.

In another embodiment, devices and methods of the invention comprise evaluation of PRO data or metadata to determine whether the PRO data meets one or more evaluative indicators of trial objectives. For example, a questionnaire can be tested for its psychometric attributes in order to ensure its suitability as a measuring PRO instrument. Psychometric validation of a questionnaire includes the evaluation of reliability, validity and responsiveness using statistical methods. For example, if a questionnaire is previously validated for its usefulness in predicting a clinical outcome, its psychometric properties are evaluated when the questionnaire is translated to use with a different language group. Questions regarding functional limitation, pain intensity, concern with appearance or activity restriction can be validated as to whether the answers exhibit similar variance in comparison to the same set of questions presented in original language.

Consolidating evaluative indicators in order to construct valid, PRO data-based clinical trial endpoints can be accomplished by a statistical method known in the art, such as, but not limited to, t-test, probability value test. Poisson distribution, derivation of correlation coefficients for each item, or measuring for consistency of each question over a period of time or over a population of subjects.

In one embodiment, a method is provided to produce a clinical trial endpoint based on data collected by PRO instruments. In another embodiment, a method is provided for the design, modification and validation of a PRO-data based clinical trial endpoint. In another embodiment, a method is provided comprising use of electronic devices in undertaking the production of a PRO-data based clinical trial endpoint.

In one embodiment, a device of the invention comprises computer executable instructions which function to produce a HRQOL questionnaire that can reliably predict improved outcome of a HRQOL independent of uncontrollable variables associated with the design of a clinical trial. For example, statistical analysis is employed for vetting procedures of a HRQOL questionnaire to produce a HRQOL-related clinical trial endpoint. Such clinical trial endpoints are selected based on a statistically significant differentiating power to provide an enhanced or clear indication of improved HRQOL for a medical product which is the subject of a clinical trial. Therefore, in one embodiment, methods and devices are provided for providing statistical relevance of HRQOL questionnaires for a particular clinical trial endpoint related to a particular test medical product.

Patient Reported Outcome (PRO)

In one embodiment, a PRO instrument is used in a clinical trial to measure the impact of an intervention on one or more aspects of subjects' health status. In one embodiment, a subject's health status can be evaluated via simple or symptom level concepts (i.e., pain severity), to more complex concepts (i.e., ability to carry out daily activities), to extremely complex concepts (e.g., quality of life), which comprise a multi-domain concept with physical, psychological, and social components. PRO data generated by a PRO instrument can provide evidence of a treatment benefit from the subject's perspective. Preferably, there should be evidence that a PRO instrument, such as a questionnaire, effectively measures the particular concept that is studied. Results collected by one or more PRO instruments can be used to provide support for one or more label claims in approved medical or food product labeling, per FDA-prescribed guidelines.

In another embodiment, a PRO instrument provides a means for measuring treatment benefits by capturing concepts related to how a subject feels or functions with respect to his or her health or condition. These concepts can be expressed as life events, behaviors, or feelings. Measurable concepts by PRO instruments can be either self-evident, such as walking, or non-observable, or known only to the subject, such as feeling depressed.

In another embodiment, a PRO instrument can be employed to support one or more clinical trial endpoints. In one embodiment, a PRO instrument is designed to effectively measure a potential label's claim of a benefit of a medical product to an intended subject population. In one embodiment, PRO data referring to a subject's symptoms or ability to function can be recorded by a PRO instrument. In another embodiment, PRO data can be analyzed to: determine characteristics of the disease, condition or syndrome treated by a medical product in a clinical trial; identify a label claim domain; identify a target subject population that can benefit from the medical product; identify a clinical trial endpoint in support of a label claim; or modify a PRO questionnaire to increase the validity of the data obtained with it.

In another embodiment, a PRO instrument is designed to test whether clinical trial results provide support for a simple label claim, such as showing an improvement of a symptom, or to provide an answer to a domain-specific question. PRO instruments can also be designed to support a more complex label claim, such as a label claim that is best substantiated by multi-domain support. In one embodiment, a PRO questionnaire is designed to address questions directed to more than one domain to delineate a subject's ability to function or a subject's psychological state. For example, a question is formulated to address how the improvement of a symptom is translated to specific clinical trial endpoints, such as an ability to perform a specific task, usually chosen from one of the subject's daily routine activities. Questions can also be directed to formulate quantifiable and measurable clinical trial endpoints showing an improved psychological state.

In another embodiment, a PRO instrument is used for capturing treatment effects that are known only to the subject, revealing the subject's perspective about the effectiveness of a treatment to health care providers, and providing a chance for systematic assessment of the subject's perspective. Such systematic assessment can provide valuable information that can be lost when that perspective is filtered through a clinician's evaluation of the subject's response to clinical interview questions. Representative examples of PRO concepts that can be measured by PRO instruments are pain, feeling, and clinically meaningful improvement in contrast to improved physiological data. These concepts are typically difficult to measure by other approaches as there are no physical, non-subjective measures for these concepts. Specifically, pain relief or pain intensity is a key aspect for an evaluation of an analgesic product. However, there are typically no observable or physical measures for these concepts. In one embodiment, a PRO instrument is designed to support a medical clam for a pain relief medication that indicates increase in the duration of period actively engaged in daily activity.

In another embodiment, a PRO instrument is used to measure PRO concepts such as seizure frequency, depression, heart failure, angina, asthma, urinary incontinence, rheumatoid arthritis, frequency of a condition, severity of a condition, sleep apnea, sexual dysfunction, anxiety, worry about getting worse, having to avoid certain situations, feeling different from others, improvement in physical function, psychological well-being, treatment satisfaction, response to side effects, or health-related quality of life measures. Measurable PRO concepts can be global, disease-specific, condition-specific, treatment-specific, population-specific, impact of a condition to daily activity, overall state of health, satisfaction with treatment or preference for a treatment, adherence to a treatment, or a subject's own evaluation on the overall state of a condition. PRO measurements can occur as an event takes place, at a regular interval, or at randomly chosen moments of time.

In another embodiment, a PRO instrument is used to measure a single concept or multiple concepts. One or more items, such as a question, can be used to support a single concept. Multiple items can be used for multiple domains within a single concept. In evaluating the usefulness of each item, all items can be equally weighted or assigned to variable weights. In evaluating a multi-domain PRO concept, each domain can be equally weighted or assigned to variable weights. In scoring each item, a single rating can be used, i.e. a score from 1 to 10 (such as 1, 2, 3, 4, 5, 6, 7, 8, 9, 10). Indexed rating, which uses multiple ratings of related domains or independent concepts, can be used. Profiling, which is multiple uncombined scores of multiple-related domains, can be employed. Battery scoring, which is multiple uncombined scores of independent concepts, can be employed for scoring and evaluation. To evaluate an overall balance of PRO instruments, a composite of index score, profile score, and battery score can be utilized.

In another embodiment, a PRO instrument is developed by the following steps. First, concepts that are relevant to a clinical trial or to potential subjects to be enrolled in the clinical trial are identified and the domains associated with the concepts are delineated. Based on the identified concepts, a conceptual framework is produced in which one or more variables, such as characteristics of the subjects to be enrolled in the clinical trial, mode of application of the PRO instrument, or expected relationships among various concepts are outlined and examined. Second, items are generated based on the conceptual framework. Methods of administrating the items are chosen. Decisions are made on the response scale of each item (i.e. how broad or narrow a scale should be), recall of item (time lapsed from the time of event to the time of recording), and frequency of presentation of item to subjects. An instruction to subjects as how to respond in general is also drafted and vetted by rounds of presentations to a test population. Procedures for scoring, such as frequency and administrative aspects of scoring, rounds of pilot tests and the manner of pilot tests, are decided. A portable electronic device, preferably a hand-held device, can be selected for the presentation of a PRO instrument (e.g., a questionnaire) to a subject. The PRO instrument can be modified and refined through pilot tests for its clarity, ease of use, and accessibility. Third, once PRO data is collected, an assessment is made on each item in terms of score reliability, validity, ability to detect change, and administrative and respondent burden. Based on the assessment, items are added, edited, deleted, or revised. When the difference in scores is minimal, the scores are assessed to identify what constitutes a meaningful difference. Statistical algorithms can be employed to find a score or a range that defines a meaningful difference in clinical outcome. Such a score or range can be used as tentative clinical trial endpoints. PRO instruments for administering PRO questions can be reformatted to present the questions in different ways. Training materials for administrators are vetted based on inputs from the subjects. PRO data collection can then be repeated with a modified PRO instrument. Fourth, based on the results obtained from modified PRO instrument, the measured concepts, study population applicability of concepts, instrumentation or method of administration are adjusted. As a last step, clinical trial endpoints that can correlate reliably to the objectives of clinical study are elucidated.

In one embodiment, PRO data collection is accomplished by an in person interview, paper-based query, electronic query, web-based query, or interactive voice response query. The comparability among the different modes of administration can be evaluated by employing one or more methods of administrations and comparing the scores obtained from each mode of administration.

In one embodiment, the PRO data collection period is modified based on the need of population. For example, for an aged population, PRO data collection can occur at the time an event takes place as to avoid a long period of memory recall, which can contribute to inaccuracy of the data. The collection period can be deliberately set to a marked event, such as a visit to a clinic. For example, a subject can be required to record PRO data just prior to the visitation and soon after the visitation.

In one embodiment, PRO data collection acquisition employs a HRQOL questionnaire that comprises questions to detect a false sense of well-being. For example, for addressing whether a subject can perform normal daily activities, two questions can be asked; whether or not a respondent can perform daily activities; and whether or not a respondent can perform a specific task, such as eating, and if so, with how much difficulty. A respondent can score highly on the question asking whether he or she can perform daily activities, but can not score well on the second question.

In one embodiment, a PRO instrument response format can be a visual analog scale (VAS), anchored or categorized VAS, Likert scale, or a generic rating scale in which patients or subjects are asked to choose the response that best describes their state or experience, event log, pictorial scale, checklist or a combination thereof.

In one embodiment, a PRO instrument can be evaluated for the level of cognitive responsiveness or literacy level of subjects. An interview or a transcript of an interview can be used to gauge a subject's level of understanding and be used as a basis of item modification. Other variables that can be considered and evaluated include appearance of PRO instrument, length of questionnaire or interview, font size, length of instruction, sentence structure, word choice, level of technical knowledge required to understand the condition a question is addressed to age of intended population, privacy settings, and perception by subjects that certain answers are appropriate or expected.

In one embodiment, criteria can be employed to test the validity of PRO instruments. For testing the validity of a scoring range, items showing highly skewed response (e.g. all subject responses scoring at the highest end of range) are modified. If a subject responds to a question by answering that none of the choices are applicable or correctly reflect his or her state of health, such questions are modified. Questions that generate an evenly distributed pattern over the range can be excluded as they can lack a significant level of discriminating power. Questions generating no variance, i.e. all subjects or respondents give the same answer, can be excluded or modified. For questions designed to reflect a change in symptom, feeling or mood, observations of subjects by a clinician and comparison of the impressions or recordings by the clinician to PRO reporting of the subject as a test of validity, can be involved. If a question fails to capture a change obviously observed by the clinician or an interviewer, the question can be modified. Items that produce unstable responses over a period of repeated tests can be assessed to increase their reliability. Items that do not correlate with other items in the same domain or concept of interest can need to be removed or revised.

In one embodiment, a statistical analysis is employed to analyze the PRO data. For example, to delineate a clinically meaningful difference, standard deviation, t-test, probability value test, or Poisson distribution is calculated to gauge a statistically significant difference. A variety of statistical methods can be applied to a set of PRO data to demonstrate concordance among different methods in order to suggest that an observed difference can be significant.

In one embodiment, a PRO instrument is used in a double-blinded, randomized clinical study. PRO instruments can also be used where blinding is not feasible, such as in then evaluation of a medical device.

In another embodiment, a PRO instrument employs a design where a subject cannot access his or her own previous answer in order to prevent bias in the answer. A portable electronic device can be configured to not permit access to a previous answer, while also not having the ability to delete or modify the answer while allowing multiple chances for answering the question.

In another embodiment, to determine whether a question produces PRO data useful as an evaluative indicator for trial objectives, the question can be tested for its suitability for use in measuring a PRO instrument in terms of its psychometric attributes. In one embodiment, the question is part of a questionnaire. Psychometric validation of a questionnaire includes the evaluation of reliability, validity and responsiveness using statistical methods. For example, if a questionnaire is previously validated for its usefulness in predicting a clinical outcome, such as an indexed measure of foot pain, its psychometric properties are evaluated when the questionnaire is translated for use with a different language group. Questions regarding functional limitation, pain intensity, concern with appearance or activity restriction can be validated as to whether the answers exhibit similar variance in comparison to the questions written in the original language.

Heath-Related Quality of Life (HRQOL)

In one embodiment, a PRO instrument or method of the invention provides and assesses a subject's HRQOL by analyzing PRO data. In one embodiment the PRO instrument is used in a clinical trial designed to determine if a medical product produces a clinical outcome that supports a specific label claim for the medical product. In one embodiment, the PRO instrument comprises a HRQOL questionnaire that provides a multidimensional assessment of a subject's well-being. In one embodiment, the HRQOL questionnaire measures qualities of a subject's life that are important to the subject and are related to a subject's disease, condition, syndrome, symptom or sign.

In one embodiment, measurements of a subject's HRQOL complements physiological measurements of a subject's response to a medical product. In another embodiment, measurements of a subject's HRQOL provide information regarding the utility of a medical product to a particular subject or class of subjects, such as how a specific treatment will affect a subject's or subjects' daily routine. Areas where an HRQOL measurement is useful include, but are not limited to, pain measurement, psychological response measurement, assessment on mobility or range of bodily motion, and assessment on social modality, such as speech, hearing, dependency to others, sleep, reading and writing.

In another embodiment, a PRO instrument can comprise one or more HRQOL questionnaires made up of a number of items or questions. These items are added up in a number of domains, sometimes called dimensions. A domain or dimension refers to the area of behavior or experience subjected to the measurement. A physical function domain can include mobility and self-care. An emotional-function domain can include depression, anxiety, and well-being. Another example of domain frequently measured for HRQOL is a social domain in which a subject's expectation, perception, experience, or feeling in social setting is measured. The HRQOL questionnaire can be rigorously evaluated by the methods disclosed herein and the importance of each item can be rated in relation to the others. Items can also be equally weighted, assuming that their values are equal.

In one embodiment, an HRQOL questionnaire can be useful for measuring the impact of chronic disease. Physiologic measures provide information to clinicians but are of limited interest to subjects; they often correlate poorly with functional capacity and well-being, the areas in which subjects are most interested and familiar with. In subjects with chronic heart and lung disease, for example, exercise capacity in the laboratory is weakly related to exercise capacity in daily life. An HRQOL questionnaire is also useful to delineate and enumerate the commonly observed phenomena in a more quantitative and measurable term. Two subjects falling within the same clinical criteria often exhibit dramatically different health-related attributes. For example, two subjects with similar ranges of motion and similar ratings of back pain can exhibit different physiological or emotional well-being. For example, some subjects with back pain can continue to work without major depression while others can have major depression and show difficulty in continuing daily activities.

In another embodiment, an HRQOL questionnaire can be utilized for the determination of medical interventions by a health administrator. For example, health administrators are interested in HRQOL for several reasons. In one embodiment, members of a heterogeneous population of subjects can respond differently or have different expenditure patterns in regards to a medical product. For example, while two groups of subjects within a heterogeneous population of subjects can respond equally well a medical product and can show improvement in clinical signs or symptoms, only one group of subject's HRQOL may show improvement. Such information can be valuable to health administrators to determine how to effectively manage health care expenditures. For example, a health administrator may find it only medically necessary to prescribe counseling to a group of subjects with a low HRQOL and not medically necessary to prescribe counseling to a group of subject with a high HRQOL. This choice by the health administrator would conserve financial resources in comparison to the costs of prescribing counseling to both groups. In another embodiment, a health administrator can incorporate HRQOL questions into existing assessments of medical products in order to measure quality of care or effectiveness. In another embodiment, insurance companies can use HRQOL information to inform reimbursement decisions.

In another embodiment, an HRQOL questionnaire can be administered either by trained interviewers or self-administered by a subject. Trained interviewers can or can not have health-related education. Administration by an interviewer can be employed where extensive resources are available, such as when it is required by a clinical trial, or mandated by government regulations. The interview can be face to face or over the phone. A self-administered HRQOL questionnaire can be employed whenever a PRO device is an appropriate platform of administration. In another embodiment an HRQOL questionnaire can be self administered by a subject with some monitoring or supervision by an interviewer. For example, a self-administered HRQOL questionnaire can be answered under the supervision of an interviewer, either under direct supervision or indirect supervision through electronic monitoring. In another embodiment, a subject can undergo training or utilize assistance when before or concurrent with the completion of an HRQOL questionnaire in one embodiment, the training or assistance can be an in-person training session, a training video, a phone number, an on-line chat connection, an instant-message connection or email assistance. In another embodiment, methods of administering HRQOL questions can be adjusted and customized for each HRQOL question to collect PRO data that can be used for delineating significantly reliable clinical trial endpoints.

In another embodiment, a surrogate system for the administration of a HRQOL questionnaire can be used in obtaining PRO data. For example, when a subject is able to answer questions but is too ill to complete a questionnaire, a surrogate person can be used to respond on behalf of the subject. The surrogate response can be tested in a pilot study by examining correlative values of the response collected among different surrogates. For example, under an experimental setting, multiple surrogates are employed to record responses from a given subject, and the answers are scored and statistically evaluated for correlation among surrogates. Questions that exhibit a greater degree of deviation among surrogates can be modified to reduce the deviation and make the data reflect a more accurate statement of the subject. Attention is also given to evaluate whether questions can be uncomfortable for dictating to a surrogate depending on the age of the surrogate, gender of the surrogate, relation of the surrogate to the subject, or other relationship factors. A surrogate system can be used partially to capture questions regarding physiological domains, such as hours of sleep, number of meals, feeling of vigor while questions of emotional domains are pursued by other means, such as an interactive display device or an interactive voice capturing device.

In one embodiment, the scoring or statistical treatment of PRO data can be performed using various scoring methods known in the art. In one embodiment, the Karnofsky score can be used. The Karnofsky scale runs from 100 to 0, where 100 represents perfect health and 0 is death. The score can be represented as a number, a decimal or a percentage. In one embodiment, the Karnofsky scale is represented by percentages. In this scale, 100% is normal, no complaints, no signs of disease; 90% is capable of normal activity, few symptoms or signs of disease, 80% is normal activity with some difficulty, some symptoms or signs; 70% is caring for self, not capable of normal activity or work; 60% is requiring some help but can take care of most personal requirements; 50% is requires help often and requires frequent medical care; 40% is disabled and requires special care and help; 30% is severely disabled and hospital admission is indicated but no risk of death; 20% is very ill, urgently requiring admission and supportive measures or treatment; 10% is moribund, rapidly progressive fatal disease processes; and 0% is death. Once informed of the scale, a subject can be given some latitude to express their feeling in using any form of numeric expression that the subject chooses to use.

In another embodiment, the Eastern Cooperative Oncology Group (ECOG) score is used to score PRO data. The ECOG score, also called the World Health Organization (WHO) score, runs from 0 to 5. In ECOG scoring, 0 denotes asymptomatic state, 1 is symptomatic but completely ambulatory, 2 is symptomatic with less than 50% in bed during the day, 3 is symptomatic with more than 50% in bed, but not bed bound, 4 is bed bound and 5 is death.

In another embodiment, the Hamilton Anxiety Scale (HAS) is employed for scoring of anxiety level of PRO data. The Hamilton Anxiety Scale (HAS) includes 14 items, each scoring from 0 to 4. The evaluation of the presence and intensity of different items is based on the subject's condition in the last 3-7 days. The total score ranges between 0 and 56. A score less than 5 indicates lack of anxiety, between 6 and 14 mild anxiety and more than 15 a clinically significant level of anxiety.

In another embodiment, the Hamilton Depression Rating scale (HAM-D) is used in a PRO instrument for recording and measuring the prevalence and the intensity of specific symptoms of depression. It includes 21 items; the first 17 are considered for the score calculation. The cut-off scores, established on the basis of many clinical studies, are as follows: 0-7 no depression, 8-15 mild depression, more than 16 moderate to severe depression.

In an embodiment, for measuring pain, the Visual Analogue Scale (VAS) scoring method can be employed to measure PRO data. It includes 10 items, such as a colored or numbered rectangular box, laid out in a row. The coloring or numbering scheme is designed in a way a subject can intuitively understand that each color or number represents an increment of pain from mild to severe episode.

In one embodiment, an observational scoring system can also be employed for administering a PRO instrument to subjects who either has trouble expressing them, or can not express their experienced quality of life verbally, such as children. For example, the Lanksy method can be used. In the Lansky method of observational scoring, 100 is fully active and normal, 90 is minor restrictions in strenuous physical activity, 80 is active, but tired more quickly, 70 is greater restriction of play and less time spent in play activity, 60 is up and around, but active play minimal; keeps busy by being involved in quieter activities, 50 is lying around much of the day, but gets dressed; no active playing participates in all quiet play and activities, 40 is mainly in bed; participates in quiet activities, 30 is bed bound; needing assistance even for quiet play, 20 is sleeping often; play entirely limited to very passive activities, 10 is neither playing nor getting out of bed and 0 is unresponsive.

In one embodiment of the invention, a PRO instrument comprises an HRQOL questionnaire designed to differentiate between subjects who have a better HRQOL score and those who have a worse HRQOL for a given medical intervention. To enable such discriminatory power, a set of HRQOL questionnaires is tested with a population over time and to see if the questionnaire can capture the change, either in physical or in emotional domain, of a subject's experience. Once proven to capture the change, the HRQOL questionnaire can be used to test whether a given medical intervention can have an ability to endow a high HRQOL score to a group of subjects with certain characteristics. In such a questionnaire, a clinical trial endpoint can be reached when a designated HRQOL score is reached or a subject provides specified answers to certain questions in a HRQOL questionnaire. In one embodiment, the subject is unaware of what answers or HRQOL score signify that a clinical trial endpoint has been reached.

In another embodiment, an HRQOL questionnaire is capable of differentiating between subject groups with high scores from low scores, which can be useful for supporting a label claim of a medical product. For example, in comparing two drugs, both treating anemia, both drugs can have similar efficacy in restoring or demonstrating physiological indication of restoration of normal range of hematocrit. However, the two drugs do not produce similar results in improving health-related quality of life. An HRQOL questionnaire designed with clear differentiation power can be used to support the label claim for a medical product that enhances or improves a subject's health-related quality of life.

In further embodiments, an HRQOL questionnaire can contain various instruments of measurement. For example, to measure reliability of the questionnaire, or to demonstrate its reproducibility and overall signal-to-noise ratio, questions can contain items that are expected to incur more or less the same responses from subjects. To measure changes or events, the questionnaire can contain items that are expected to be responded differently by subjects with a small change of physical or mental state.

In another embodiment, an HRQOL questionnaire can be designed to verify the validity of the answers provided. For example, to reduce the margin of error of each question as well as to validate the reproducibility of each answer, questions can be repeated in different forms, presented with different levels of comprehensiveness, deliberately biased to test the level of scrutiny of the reader, or presented with different levels of simplicity and clarity.

In one embodiment, an HRQOL questionnaire can be used in a clinical trial, to measure primary and secondary outcomes. As a tool for measuring primary outcome, for example, HRQOL questions can be designed for a disease-specific measure if no other outcomes exist that are directly clinically relevant to the subject. Another example of using an HRQOL questionnaire as a primary measuring tool is to design a questionnaire specifically for subjects with chronic disease and show that a medical product under test is effective to improve HRQOL in subjects. As a tool for measuring a secondary outcome, an HRQOL measurement can be used to supplement physiological response measures in a study of a new medical product.

In one embodiment, measurement of a subject's HRQOL can also be used to obtain a more comprehensive picture of the impact of medical intervention. For example, a comparison among various anti-hypertensive agents can be made by employing an HRQOL measurement. Although the agents in comparison can exhibit similar efficacy in treating hypertension, an HRQOL measurement in the area of feelings of well-being, physical function, emotional function, sleep, sexual function, and side effects, can show that antihypertensive agents have a differential impact on many aspects of HRQOL.

In one embodiment, measurement of a subject's "global" (also known as generic) HRQOL can be employed to provide complementary information about the range and magnitude of a medical product's effect on a subject's overall HRQOL. In one embodiment, measurement of a subject's global HRQOL can identify the existence of a subject's adverse that would not be detected by only measuring a subject's specific HRQOL. If the efficacy of an intervention is already known, a clinical trial that measures a subject's global HRQOL can attempt to elucidate the full impact of a treatment on a subject's quality of life. Utility measures addressing economic implications of an intervention can be a useful venue for global measure of HRQOL. For example, a cost analysis per quality-adjusted life-year gained can provide information valuable for subjects with chronic disease.

In another embodiment, measurement of a subject's global HRQOL can be used for gauging the trade-off between the length of a subject's life or length of a subject's disease remission and subsequent quality of life. Such situations can arise in chemotherapeutic treatments for malignant disease or anti-viral treatment for subjects with human immunodeficiency virus (HIV) infection. For example, in a clinical trial of zidovudine for mildly symptomatic HIV infection, the drug increased the period of progression-free survival by an average of 0.9 months. However, when disease progression or severe adverse events were counted as negative outcomes in a "quality-adjusted: time without symptoms or toxicity" test, subjects treated with zidovudine did poorly, suggesting that the HRQOL perspective can impact treatment decisions.

In another embodiment, measurement of a subject's specific HRQOL can be used to provide information about the range and magnitude of a medical product's effect on one ore more specific aspects of subject's HRQOL. In one embodiment, a specific HRQOL measurement for a subject's level of pain can be determined in a clinical trial involving administration of a pain relief drug. In another embodiment, a specific HRQOL measurement for a subject's frequency of urination can be determined in a clinical trial involving administration of a drug for treatment of urinary tract infections. In another embodiment, a specific HRQOL measurement for a subject's feeling of breathlessness can be determined in a clinical trial involving administration of a drug for treatment of asthma.

Development of Clinical Trial Endpoints

In one embodiment, a clinical trial endpoint (e.g., clinical endpoint or surrogate endpoint) is developed through the endpoint development process (EDP), which is a multi-step method for evaluating, determining, and building a PRO measurement strategy for implementation into clinical trials. The first step in the EDP is to develop a Conceptual Model. A conceptual model is a framework for understanding the relevant outcomes for a program of research. It informs the selection and/or development of clinical trial endpoint measures and it delineates the rationale for what needs to be measured. In order to successfully achieve a Conceptual Model, it is useful to specify the following: a prioritized list of goals and/or label claims; the relevant subject population; the mechanism of action or relevant drug action(s) of the treatment or intervention; and the relevant concepts or treatment outcomes of interest.

The next step in the EDP is Concept Justification. Concept Justification includes activities to evaluate the evidence supporting the relevance and importance of a specified measurement concept. Moreover, these activities allow a researcher to substantiate the decision to include a specified measurement concept within a given clinical program from the perspective of subjects, experts, payers, and the empirical literature. A Concept Justification provides the evidence supporting the relevance and importance of specified concepts and also informs the feasibility of measuring those concepts. A Concept Justification substantiates the selected measurement concepts via the following sources of input: expert input, subject reports, empirical evidence, and payor relevance. Obtaining expert input can include workshop contributions, conclusions from published review papers, and knowledge gained during meetings with a Key Opinion Leader or KOL. Empirical evidence can include results from the published scientific literature, professional presentations, and unpublished internal study results. Support from subject interviews can include results drawn from qualitative subject interviews and establish the content validity of a concept and the clinical meaningfulness of scores produced by the PRO instrument assessing that concept. Payor relevance reflects the extent to which a payor is likely to pay for a medical product based on its ability to effectively accomplish a specified concept. A Concept Justification also allows for a prioritization of measurement concepts within a given clinical program. A hierarchy of concepts intended to support one or more label claims can be used. In one embodiment the Concept Justification comprises a can be documented as: a concept specification and description; a concept justification matrix; and a concept justification knowledge base.

The next step in the EDP is to develop a measurement strategy. A measurement strategy describes the measurement approach to optimally and effectively assess the selected effective concepts and can include recommendations on the following: the focus of assessment or the particular aspects of assessment (e.g., severity, frequency, duration of a symptom-level concept); interval of assessment (or the time between unique assessments); recall period (or the period of time over which subjects are asked to evaluate and report on their experiences); schedule of assessments (or how often an assessment should occur); and timing of assessment (or when or what time point an assessment should occur). A Measurement Strategy informs the selection and/or modification of existing PRO instruments or decision to develop new ones. In other words, the Measurement Strategy provides a point of comparison among currently available PRO instruments built to measure a specified concept to a document outlining how that concept should optimally be measured relative to scientific and regulatory guidelines. In the event that no PRO instrument is available to measure the specified concept in a way that is consistent with the measurement strategy, the measurement strategy can be used to inform the development of a new PRO instrument.

The next step in the EDP is PRO instrument identification and evaluation. In one embodiment the PRO instrument is identified and evaluated after a concept has been specified and an optimal measurement strategy has been articulated. PRO instruments can be evaluated in the context of the articulated Measurement Strategy to determine whether they are designed to measure the specified concept in the ways that are recommended; if there are existing PRO instruments capable of measuring the specified concept in the ways articulated in the Measurement Strategy, these PRO instruments can be selected for use in clinical trials; if there are existing PRO instruments capable of measuring the specified concept but not necessarily in the ways articulated in the Measurement Strategy, these can potentially be modified for use in clinical trials; if no existing PRO instruments can be identified to evaluate the specified concepts in ways consistent with the Measurement Strategy, alternate Measurement Strategies can be considered at this time; if no existing PRO instruments can be identified to evaluate the specified concepts in ways consistent with the Measurement Strategy, the creation and evaluation of new PRO instruments can also be considered at this time.

The next step in the EDP is developing a Conceptual Framework. A Conceptual Framework provides a description of the concepts that underlie a label claim in terms of the Measurement Strategy and/or the PRO instruments and items employed or used to assess the specified concept. A Conceptual Framework can be substantiated via theoretical or logical evidence. For example, for a researcher to demonstrate content validity of a conceptual framework, the research can make logical links between label claims, the concepts that underlie those label claims, and the Measurement Strategy or PRO instruments that measure whether a medical product can produce an outcome that supports a label claim. A Conceptual Framework can also be substantiated via empirical validation evidence. Typically, a researcher must demonstrate that a Measurement Strategy or PRO instrument produces scores that are valid, reliable, and responsive to actual change in the specified measurement concept of interest.

The final step in the EDP is to develop a clinical trial endpoint model. The clinical trial endpoint model specifies the hypothesized relationships among all treatment benefit clinical trial endpoints intended to test one or more label claims. Setting it apart from the conceptual framework is that the clinical trial endpoint model not only specifies the actual clinical trial endpoints, but it does so in a hierarchical fashion.

In one embodiment of the present invention, a method of the present invention may be incorporated in computer-executable instructions recorded on a computer readable medium suitable for use in an electronic device, such as a computer, computer network server or a portable electronic device. The computer readable can include, for example, a hard disk, RAM medium, diskette, CD-ROM or other optical or magnetic storage medium. The computer-executable instructions can optionally be stored on a server that can be remote from a subject and/or clinical staff member.

In another embodiment, a PRO instrument is incorporated in computer-executable instructions recorded on a computer readable medium suitable for use in an electronic device, such as a computer, computer network server or a portable electronic device. A computer readable medium can be an optical disc (such as a CD-ROM or DVD-ROM), a recordable disc, a floppy disk, a hard disk, solid sate memory, Random Access Memory (RAM) or Read Only Memory (ROM). In one embodiment the computer readable medium is located in a portable electronic device. In one embodiment a PRO instrument recorded on a computer readable medium suitable for use in a portable electronic device comprises one or more HRQOL questions. In another embodiment the PRO instrument is a HRQOL questionnaire. In another embodiment the PRO instrument includes computer-executable instructions for the collection of PRO data or metadata.

In one embodiment, a PRO instrument is developed and utilized in constructing a clinical trial endpoint. In one embodiment the PRO instrument comprises one or more HRQOL questions. In another embodiment the PRO instrument is a HRQOL questionnaire. In this embodiment three phases are involved in constructing one or more clinical trial endpoints: creation of an HRQOL question; verification of an HRQOL question for use in a PRO instrument that is implemented on a PRO device; and acquisition of PRO data or metadata (such as by using the PRO device to administer the PRO instrument to a subject) and construction of one or more clinical trial endpoints based on review of the PRO data or metadata. In one embodiment, the PRO device is a portable electronic device. During the creation phase, an HRQOL question is developed by one or more methods described herein. In one embodiment, a question can be developed 201 according to the EDP. The HRQOL question can then be converted to a computer-executable instructions 202. The HRQOL question is implemented in a PRO device by installation of computer-executable instructions 203. The question can be implemented alone or as part of a questionnaire. During the verification phase, each HRQOL question is tested for whether it meets one or more evaluative indicators to assess its ability to measure clinical outcomes. PRO data or metadata collection is performed with a PRO device 204. The PRO data is then analyzed for data validity, ability to detect change in patient's response, administrative burden, respondent burden, and regulatory compliance 205. Depending on the result of analysis, a decision is made regarding the HRQOL question's meets one or more evaluative indicators 206. There is a feed-back loop sending an unqualified question back to the creation phase for revision and/or recreation of the question and PRO device implementation. The feed-back loop serves to enhance and improve each HRQOL question 212. A HRQOL question, once qualified as demonstrating a capacity as an evaluative indicator, is retained and collected with other qualified questions for final implementation 207 during which a PRO instrument comprising a collection of qualified HRQOL questions is implemented in a PRO device 208. During the acquisition phase, the PRO device, comprising a set of validated questions is employed in collecting PRO data 209. The collected data is analyzed according to the evaluative indicators 210. Based on the PRO data analysis, one or more clinical trial endpoints is constructed 211. The collected data can show an expected or an unexpected outcome of the subject of a clinical trial. For example, PRO data analysis can reveal previously unappreciated benefit or side effect associated with a medical treatment. In one embodiment the PRO data analysis includes using metadata collected about the PRO data to analysis the validity or reliability of the PRO data.

In one embodiment, PRO data or metadata is collected and processed by an electronic system as shown in FIG. 1. A process is provided wherein a bilateral flow of information between a processor which is implemented with computer-executable or processor-executable instructions and a database, between the processor 103 and a portable electronic device 101, between the processor and input 104/output device 102, and between the processor and one or more databases 105, 106 enable processing of PRO data to determine if it meets one or more evaluative indicators. In one embodiment a clinical trial endpoint is constructed by consolidating results obtained from analyzing the PRO data by determining, in part, if the PRO data meets one or more evaluative indicators. Flowing of information to and from the processor can be accomplished over a hard-wire connection or over a wireless connection if the processor is housed in a place or a unit physically separated from other devices, such as input/output device, databases, or portable electronic device. Consolidation of evaluative indicators can be performed by statistical, mathematical or logical operation of two or more evaluative indicators. Consolidation can also be performed by manual evaluation of indicators by an operator experienced with evaluation of PRO data. An example of a person skilled in the evaluation of PRO data would include a person familiar with a formation of a health questionnaire, such as an HRQOL questionnaire. A statistical program or a data mining program can be employed to spot recording error, invalid data point or data outliner and exclude them in formulating clinical end points. The processor is provided and is adapted to communicate with at least one database. The database can store data related to PRO data or metadata and instructions to respond to PRO data or metadata. An example of a database is described in U.S. Patent Application 20050009862. An input device is provided to allow the subject or other person to provide input to the processor. The input device can be a keyboard, a touch screen, a mouse, a modem or other such device adapted for communication with the processor. An output device is also preferably provided to receive and display information from the processor. Examples of output devices include a printer and a monitor.

In one embodiment of the invention, a portable electronic device is provided and can be coupled to a processor. In one embodiment, the portable electronic device can comprise an alarm, an input device, an output device, and/or a database. In one embodiment a portable electronic device is a Palm Pilot by Palm, Inc.

In another embodiment, a portable electronic device is an Acer C500 series(integrated GPS) such as, c510, c530, c531, and Ferrari Racing, Acer N series such as, n10, n30, n50, n35 (integrated GPS), n300, n310, n311, and n320, ASUS series such as, MyPal A600 1, MyPal A620, MyPal A620BT, MyPal A626, MyPal A632, MyPal A636, MyPal A636N, MyPal A632N, MyPal A639, MyPal A686, MyPal A696, MyPal A716, MyPal A730, MyPal A730W, P505, P525, P535, P735, and P565, Audiovox series such as, Thera—Pocket PC with Built-In CDMA Verizon cellphone, PPC-6600/6601— Blackberry series such as 850, 957, 6710, 6750, 7000, 7100, 8700, 8800, 8100, 8300, 9000—HTC Harrier (CDMA), PPC-6700—HTC Apache (CDMA), PPC4100—GSM/GPRS Pocket PC Phone, PPC-6800—HTC Mogul (CDMA), and PPC-6900—HTC Touch (CDMA), Binatone Carrera (GPS) series such as, X350, and X430, Cassiopeia series such as, BE-300, E-100, E-115, E-125, EM-500, and A-22T, Compaq's PC Companion, Cowon's Cowon Q5W, E-TEN series such as, M6002, G5003, X500 glofiish4, M700 glofiish5, T5006, and X800 glofiish7, Dell series such as, Dell Axim, Axim X308, Axim X59, Axim X5010, Axim X50v11, Axim X5112, and Axim X51v13, Dopod series such as, Dopod Site 14, Dopod C500 15, Dopod C730 16, Dopod HTC Touch 17, Dopod D600 18, Dopod M700 19, Dopod C720 20, Dopod 838 Pro 21, Dopod 818 Pro 22, Dopod C800 23, Dopod P800W 24, Dopod D810 25, Dopod U1000 26, Dopod 595 27, and Dopod 300 28, Fujitsu series such as, Pencentra 13029, and Pencentra 20030, Fujitsu-Siemens Computers series such as, Pocket LOOX 600, Pocket LOOX 610BT, Pocket LOOX 610BT/WLAN, Pocket LOOX 410, Pocket LOOX 420, Pocket LOOX 710, Pocket LOOX 718, Pocket LOOX 720, Pocket LOOX N500, Pocket LOOX N520, Pocket LOOX N560, Pocket LOOX C550, Pocket LOOX N100, Pocket LOOX N110, Pocket LOOX T810, and Pocket LOOX T830, Garmin series such as, iQue M5 31, iQue M4 32, and iQue M3 33, Hewlett Packard series such as, Jornada, Jornada 520 series, Jornada 540 series, Jornada 560 series, Jornada 680 series, Jornada 690 series, Jornada 710, Jornada 720, Jornada 728, and Jornada 820 handheld, HP/Compaq iPAQ series such as, H1900, H1910, H1920, H1930, H1935, H1940, H1945, H3630, H3670, H3760, H3850, H3870, H3950, H3955, H3970, H3975, H4150, H4155, H5550, HP2210, HX2110, HX2400 Series, HX2795, HX2795b, HX4700, HX4705, RX1950, RX1955, RX3115, RX3715, RX5910, RZ1715, and hw6500 Series, Hitachi's Hitachi G1000, HTC series such as, HTC Advantage X7500/HTC Athena, HTC Advantage X7501/HTC Athena, HTC Advantage X7510, HTC Alpine, HTC Amadeus, HTC Apache, HTC Artemis/HTC P3300, HTC Atlas/HTC P4351, HTC Blue Angel, HTC Breeze/HTC MTeoR, HTC Canary, HTC Cavalier/HTC S630, HTC Census/HTC P6000, HTC Charmer, HTC Cheetah, HTC Erato/HTC S420, HTC Excalibur/HTC S620/HTC S621, HTC Falcon, HTC Faraday, HTC Feeler, HTC Foreseer, HTC Galaxy, HTC Gene/HTC P3400/HTC P3401, HTC Gemini, HTC Harrier, HTC Herald/HTC P3450, HTC Hermes, HTC Himalaya, HTC Iris/HTC S640, HTC Kii, HTC Libra/HTC 5800/HTC S720, HTC Love/HTC P3350, HTC Melody/HTC Muse, HTC Magician, HTC Monet/HTC S320, HTC Omni, HTC Oxygen/HTC S310, HTC Panda/HTC P6300, HTC Pharos/HTC P3470, HTC Prophet, HTC Robbie, HTC Rosella/iPAQ H3870/iPAQ H3875, HTC Sedna/HTC P6500, HTC Sirius/HTC P6550, HTC Sonata, HTC Startrek/HTC S411, HTC Tanager, HTC Titan/HTC P4000, HTC Tornado/HTC Tornado Noble/HTC Tornado Tempo, HTC Touch/HTC Elf/HTC Ted Baker Needle/HTC Vogue/HTC P3050/HTC P3450/HTC P3452, HTC Touch Cruise/HTC Touch Find/HTC Polaris/HTC P3650, HTC Touch Diamond/HTC Victor/HTC P3100/HTC P3700/HTC P3702, HTC Touch Dual/HTC Nike/HTC P5500, HTC Touch Find, HTC Touch HD//HTC Blackstone/HTC T8282, HTC Touch Pro/HTC Raphael, HTC Trinity/HTC P3600, HTC Typhoon, HTC TyTN/HTC Hermes, HTC TyTN II/HTC Kaiser, HTC Vox/HTC S710/HTC S711, HTC Universal, HTC Voyager, HTC Wallaby, HTC Wave, HTC Wings/HTC S730, HTC Wizard/HTC Prodigy/HTC P4300, HTC P3400i, and HTC P3600i, i-mate series such as, Momento Digital Photo Frame, Pocket PC, and Ultimate 9502, iphone, IBM's Workpad z50, JVC's MP-PV131 (never released), Jointech's J-Pro JL7100 Mini Laptop, LG's LN505 GPS Navigator, Linksys series such as, Linksys WIP-300 VoIP WiFi phone, and Linksys WIP-330 VoIP WiFi phone, Magellan Navigation series such as, Magellan RoadMate 1200, Magellan RoadMate 1412, Magellan Maestro 3100, and Magellan Maestro 4210, Meizu's Meizu M8, Mobile Crossing's WayPoint 100 including CF based GPS, and WayPoint 200 including BT based GPS, Motorola series such as, Motorola MC17, Motorola MC35, Motorola MC50, Motorola MC70, Motorola MPx200, Motorola MPx220, Motorola MPx300, Motorola i920/i930, and Template:Motorola Vip 1200, MWg series such as, Atom Life, Atom V, MWg Zinc II, MWg UBiQUiO 503g, and MWg UBiQUiO 501, NAVIGON(Personal Navigation Assistant) series such as, 7100, 5100, and 2100, NEC's Nec MobilePro, NTT DoCoMo's Sigmarion series, O2 series such as, O2 XDA, O2 XDA II, O2 XDA IIi, O2 XDA IIs, O2 XDA EXEC, O2 XDA Atom, O2 XDA Atom Executive, O2 XDA Atom Life, O2 XDA Flame, O2 XDA Orbit, and O2 XDA Stealth, Palm series such as, Treo 700w, Treo 700wx, Treo 750, Treo 755p, Treo 800w, and Treo 500, Philips series such as, Philips Nino—bar-style device with touchscreen, and Philips Velo—small-notebook-style device with monochrome display, Samsung series such as, Samsung E900, Samsung pixel, and Samsung 1780, Silvercrest's Mobile Navigation System PNA-M4310T, Siemens series such as, SX56, SX66, P1, and Siemens Sirec D300, Snap-on Tools series such as, MODIS, and Snap-on SOLUS, Sophia Mobile nani, ThinCCo series such as, Tisio 90CE 34, Tisio 95CE 35, Tisio 96CE 36, and Tisio 300CE 37, Toshiba series such as, e310, e335, e355, e400, e450, e550g, e740, e750, e800, e805, e830, g500, and g900, Unitech series such as, MR650, PA950, PA962, and PA966, UTStarcom series such as, PPC-6700—HTC Apache, PPC-6800—HTC Mogul, and PPC-6900—HTC Touch, Vadem series such as, Clio 1000, Clio 1050, and clio NXT, Viewsonic series such as, V35, V36, V37, and V38, Vivax's viaGPS 350, Yakumo's deltaX 5 BT 38.

In one embodiment, a computer algorithm employing statistical analysis technique is applied to quantitative data collected by a PRO device. Statistical analysis and other data treatment can include logistic regression, discriminant function analysis, classification and regression trees, neural networks, and multiple linear regression. Detailed descriptions of statistical technique are described in U.S. Pat. No. 6,879,970, which is herein incorporated by reference in its entirety.

In another embodiment, a computer program product is provided that comprises a computer readable medium having computer program logic encoded thereon for enabling a processor to provide a clinical trial endpoint. In one embodiment, the computer program product comprises a receiving procedure that enables a processor to receive data, from a portable electronic device. In one embodiment, the data comprises PRO data or metadata. In one embodiment, the data comprises a response to one or more questions responded to by a subject who was administered a medical product or a placebo. In one embodiment, the one or more questions are administered to the subject by a portable electronic device. In another embodiment the computer program product comprises an analyzing procedure to analyze the data. In one embodiment the analyzing procedure analyzes the data for one or more evaluative indicators. In another embodiment the computer program product comprises an output procedure to provide one or more clinical trial endpoints based on the analysis of the data.

In another embodiment, a computer program product is provided that comprises a computer readable medium having computer program logic encoded thereon for enabling a processor to provide a questionnaire for use in a clinical trial. In one embodiment the computer program product comprises a receiving procedure that enables a processor to receive data from a portable electronic device, wherein the data comprises a response to one or more questions responded to by a subject who was administered a medical product or a placebo. In one embodiment the data comprises PRO data or metadata. In another embodiment, the computer program product comprises an analyzing procedure to analyze the data to determine the validity or reliability of the question, wherein the procedure collects a question determined to be valid or reliable and outputs them for use in a clinical trial questionnaire or the procedure modifies a question determined to be invalid or unreliable and outputs them for administration to a subject who is administered a medical product or a placebo. In another embodiment, the analyzing procedure comprises analyzing the data for one or more evaluative indicators. In another embodiment, the computer program product comprises an output procedure to provide a validated or reliable question for use in a clinical trial or to provide a modified question to a subject who is administered a medical product or a placebo.

In one embodiment, a portable electronic device, a server, computer workstation or a desk top computer receives and assesses data. In one embodiment the data is PRO data. In another embodiment the data includes metadata collected about the PRO data, such as a subject's timely completion of questions or compliance with a clinical trial regimen. In one embodiment the metadata includes information on when (time or date) a subject completed a question, the amount of time a subject took to complete a question, the length of a delay before responding to a prompt to answer a question, the length of time between answering questions the number of times a subject changed an answer for a question, the content of a preliminary answer to a question where the answer was later changed, the physical location of the PRO device when a subject answered a question. In another embodiment, the PRO data or metadata is transmitted to a remote location for assessment. Transmittal can be through any conventional means for electronic transmittal of data. For example, the transmission of collected data can be performed via any route known in the art including, but not limited to, direct communicative link (e.g., by wires, circuits, or optical connections), wireless communication systems (e.g., WiFi, 3G, bluetooth, EDGE), the Internet, and Earth-orbiting satellite systems. In some embodiments, the collected PRO data or metadata is transmitted to a data analysis system, such as a remote data analysis system. In one embodiment the remote data analysis system is comprises a computer for example a desktop computer, a server, computer workstation, or other suitable computational device known in the art, including a CPU or a network interface circuit.

In one embodiment a computer system for providing a clinical trial endpoint is provided that comprises a computer readable medium having computer program logic encoded thereon, wherein the computer program logic comprises instructions. In one embodiment the computer system comprise input instructions for receiving data from a portable electronic device, wherein the data comprises a response to one or more questions responded to by a subject who was administered a medical product or a placebo, wherein the one or more questions are administered to the subject by the portable electronic device. In one embodiment the data comprises PRO data or metadata. In another embodiment the computer system comprises analysis instructions for analyzing the data. In one embodiment the analysis instructions comprise analyzing the data for one or more evaluative indicators. In another embodiment the computer system comprises output instructions for providing one or more clinical trial endpoints based on the analysis of the data. In another embodiment the computer system further comprises instructions to send information to the portable electronic device, wherein the computer system is remote from the portable electronic device. In another embodiment the information comprises one or more questions.

In another embodiment a computer system for providing a questionnaire for use in a clinical trial is provided that comprises a computer readable medium having computer program logic encoded thereon, wherein the computer program logic comprises instructions. In one embodiment the computer system comprises input instructions for receiving data from a portable electronic device, wherein the data comprises a response to one or more questions responded to by a subject who is administered a medical product or a placebo. In one embodiment the data comprises PRO data or metadata. In another embodiment, the computer system comprises analysis instructions for analyzing data to determine the validity or reliability of the question, wherein the procedure collects a question determined to be valid or reliable and outputs them for use in a clinical trial questionnaire or the procedure modifies a question determined to be invalid or unreliable and outputs them for administration to a subject who is administered a medical product or a placebo. In another embodiment, the computer system comprises output instructions to provide a validated or reliable question for use in a clinical trial or to provide a modified question to a subject who is administered a medical product or a placebo.

A computer or a system of computers can be specifically programmed, designed, arranged and/or manufactured to implement various embodiments described herein. A system comprising one or more devices that is custom-made for collection of the PRO data or metadata can send collected the PRO data or metadata to a separate, centralized data processing center to assess the PRO data or metadata. A distributed system of PRO data or metadata assessment can be employed to assess a large data set collected by a PRO device in which the assessment is performed by a multitude of computers operated independently of each other. A simple, wearable PRO device can be manufactured for clinical trials using a light or simple carrying device for PRO data or metadata collection. An all-in-one PRO device, wherein the device is capable of prompting, collecting, assessing, and reporting the assessed outcome to a designated server, printer, display, or a secured database can be manufactured. Various electronic components, such as a central processing unit (CPU), a graphic-user interface (GUI), a read-only memory (ROM), a random access memory (RAM), a electronic data storage device such as a hard disk, a circuit board, a cooling device such as a fan, a graphic accelerator chip, a wireless communication board, a sound card, serial or parallel port, disk controllers and data bus controllers and connectors or other electronic components typically associated with the building of a computing device can be employed in manufacturing a custom device for collection and/or processing and assessing of PRO data.

In one embodiment, a PRO device, such as a portable electronic device, allows a subject to self-administer a health-related quality of life (HRQOL) questionnaire in connection with a clinical trial. The portable electronic device can prompt the subject to record certain patient-reported outcomes (PRO) and subsequently transmit PRO data or metadata to a remote server for statistical analysis and reporting. In one embodiment, the portable electronic device's technical specifications include the following elements: a processor, a memory, a display, input/output, connectivity, a power supply and optionally, an expandable memory, a USB interface or encryption. In one embodiment, the processor provides high computing power with low power consumption. In one embodiment, the processor is at least as powerful as a 32-bit Intel or AMD processor running at a speed of 200 MHz. In another embodiment, the processor supports multiple power modes to preserve battery life. In one embodiment, the memory is RAM (random access memory) and can be used as temporary processor memory and file storage space. In one embodiment, the RAM provides at least 512 MB of memory to run systems such as the operating system, the PRO instrument (comprising the HRQOL questionnaire), and speech and recognition software. In another embodiment, the portable electronic device has a ROM Flash memory for data storage. In another embodiment, the portable electronic device has a minimum 1 GB of NAND-ROM Flash memory for storage. In another embodiment, the portable electronic device has one or more slots for external memory. In one embodiment, the external memory is an external memory card (such as CompactFlash, Memory Stick, or Secure Digital card). In one embodiment, the external memory can store updates to the HRQOL application or related applications.

In one embodiment, the portable electronic device that comprises a display having at least a 320×320-pixel resolution, which optionally support color. In another embodiment, the portable electronic device comprises a display with touch screen functionality. In one embodiment, the screen size and resolution is manufactured to ensure sufficient readability in field conditions without compromising battery life. In another embodiment, the input device comprises one or more buttons which correspond to the answer choices to each HRQOL question displayed. In one embodiment, an HRQOL application assigns a function to a button present on the portable electronic device.

In one embodiment, the portable electronic device comprises speech recognition software to allow for subject responses to HRQOL questions via built-in microphone. In another embodiment, the portable electronic device comprises an HRQOL application that comprises a text-to-speech functionality to offer voice prompts to a subject via built-in speakers.

In one embodiment, the PRO device is a portable electronic device that can connect to another computer, such as a server, by a solid state connection, such as through a USB connection, a min-USB connection, a telephone wire connection, an Ethernet connection, or a base or charger connection. In another embodiment, the PRO device is a portable electronic device that supports one ore more wireless communication protocols with a remote server to upload subject PRO data or metadata. In one embodiment, the wireless communication protocol can be a short range wireless connection such as Bluetooth and WiFi (IEEE 802.11). In another embodiment, the wireless communication protocol can be one that works by cellular (such as 3G or EDGE) or a satellite network.

In one embodiment, the portable electronic device comprises one or more encryption mechanisms to provide secure information access, storage, or communication. Encryption and cryptography installments, both in hardware encryption and in software encryption, can be included for secure interactions between the handheld and other devices. In one embodiment, the portable electronic device is equipped to support security protocols to guarantee safe operation and communication, such as Baltimore Cyber Trust Root, Baltimore Cyber Trust Root, GTE Cyber Trust Global Root, RSA Data Security, Testing ACS Root, Thawte Premium Senrer CA, Thawte Server CA, and VeriSign Class 1,2,3,4 Public Primary Certification Authority. Encryption can be achieved via software or dedicated hardware to reduce the use of processor resources used to perform encryption algorithms.

In one embodiment, the portable electronic device comprises a rechargeable battery, such as a lithium ion, a nickel cadmium, or a nickel metal hydride battery. In another embodiment, the portable electronic device has a port to receive power via USB or AC adaptor.

In one embodiment, the portable electronic device comprises a mother board. One or more CPU is placed on the board. In one embodiment, the portable electronic device comprises a processor for handling graphic input/output signals, such as NVIDIA GPU, that can be employed in parallel to a main processor element. In one embodiment, the portable electronic device comprises at least, a power supply, a wireless radio transmitter, a processor, a RAM or ROM memory and optionally, an encryption module. In one embodiment, the portable electronic device comprises a USB or mini USB port to connect with another device. Optionally, the portable electronic device comprises a Firewire port. In one embodiment, an HRQOL application comprising a questionnaire is e encoded in the RAM or ROM memory as computer-executable instructions. In one embodiment, the encoding is accomplished by installing computer-executable instructions representing the HRQOL application comprising a questionnaire on the portable electronic device's hardware as "firmware" in the device's ROM.

In another embodiment, the portable electronic device comprises at least one encryption device, power supply, and ROM or RAM connected to a mother board. Both the operating system and the HRQOL questionnaire can be encoded in the solid-state ROM flash memory device as computer-executable instructions. The encoding comprises installing computer instructions representing the HRQOL questionnaire on the portable electronic device hardware as "firmware" in the device's ROM. Upon activating the device, the operating system will load the HRQOL application into the RAM memory. In one embodiment, the HRQOL application will prompt a subject with a series of questions on a graphic display. A subject can respond to such prompts by means of input buttons (such as on a keyboard) or by interacting with a touch screen. Subject responses can be stored in flash memory until the completion of the questionnaire. The PRO data or metadata can be encrypted via a wireless radio transmitter and transmitted to a remote server for further processing.

In another embodiment, a portable electronic device begins a process of self-initialization when powered on. The portable electronic device loads a basic operating system from a built in memory (e.g., ROM) or from external memory. The portable electronic device's operating system provides for interfaces with the hardware of the unit, such as the display, subject input buttons or networking devices. Once fully loaded, the operating system in turn loads a PRO data or metadata collecting software from ROM or other memory storage. In one embodiment, the PRO data collecting software is a PRO instrument. In another embodiment the PRO data collecting software can also collect metadata.

In one embodiment, the PRO software then attempts to locate any existing PRO instrument configuration files from within a preprogrammed area of the portable electronic device's storage. If no questionnaire is found in storage, the portable electronic device informs the subject that no questionnaire could be loaded, and then puts itself into a standby state until it is connected to an administrative computer (such as a server or desktop) by a wired or wireless connection and has a PRO questionnaire installed.

In another embodiment, computer executable instructions encoding a PRO instrument is found in the portable electronic device's storage. It can be loaded from storage into RAM by the PRO software: The software can parse the questionnaire file, interpreting elements from the file such as questions to be asked, the format of answers expected, and the timing of the questions. The portable electronic device's display screen informs the subject of the title of the questionnaire and can optionally provide general information about the questionnaire such as the current time or the schedule of question prompts called for by the questionnaire. The portable electronic device then sets an interrupt to coincide with the next timed question called for by the questionnaire. The portable electronic device then puts itself into a standby state until a question interrupt indicates that there is a question from the questionnaire to be asked. The standby state involves turning off the display to conserve battery power. The portable electronic device can be woken from the standby state by the subject's action, which causes the portable electronic device to relight the screen and display the same information as on startup. After a designated amount of time without a subject's action, the portable electronic device's again returns to a standby state.

In one embodiment, a portable electronic device can respond to a question interrupt, by alerting the subject by activating an alarm and presenting on the display the question called for by the questionnaire file. In one embodiment the alarm is a flashing light, vibration, or sound. The portable electronic device then waits for the subject to read the question and enter an answer. The subject can enter an answer by any of a number of methods. For questions that use a multiple choice answer or a ranking on a scale, the subject can be presented with a set of buttons, either hardware buttons on the body of the portable electronic device or "buttons" created on the screen in software. The subject can then select the answer that describes their own experience through input via the hardware buttons or via a touch screen selection of software buttons. For questions that use long form narrative responses, a blank area is provided on the display in which the subject can write words using the touch screen and a stylus. This answer is then digitally saved in a compatible format (such as jpeg or png) in the storage of the portable electronic device. If the subject does not immediately answer the question, the portable electronic device continues to flash a light (such as an LED), periodically vibrate or make audible sounds until the subject's attention is gained and the question is answered.

In one embodiment, a portable electronic device, after a question is successfully answered, can either store the answer to the question in storage, in anticipation of returning results in batch at a later time, or it can immediately return the answer to the question to the tester, if such is demanded by the questionnaire file. If answers are returned immediately, the portable electronic device begins the process of acquiring a means of networking.

In one embodiment, a portable electronic device is configured to use a wireless Ethernet card. The portable electronic device can bring the wireless Ethernet card online before connecting to a remote server or desktop computer. The portable electronic device can send power to the Ethernet card, the operating system loads and initialize the drivers and the card will begin searching for available wireless Ethernet networks. Where the portable electronic device is programmed with information about preferred or mandatory wireless networks, those networks are searched for and, if available, configured. The portable electronic device negotiates with the wireless network and receives an IP address as laid out in the 803.xx Ethernet specifications and the IP networking specifications. Once negotiation has finished, the portable electronic device contacts an Internet host specified in the questionnaire file, create a secure FFPS (or other suitable protocol) connection and transfer the answer, along with a unique identifier, to a predetermined directory on the host. While connected, the portable electronic device can also, depending on configuration, seek to download an updated questionnaire file if one is available. If one is available, the old questionnaire file will be replaced by the new one, which will then be read into memory and its updated questionnaire program resumed. Once all network activity has finished, the portable electronic device is instructed to disconnect from any connected network, unmount the device driver and power down the wireless Ethernet card.

In another embodiment, a portable electronic device is configured to use a wireless cellular network. The portable electronic device powers on the cellular hardware, loads the appropriate drivers, obtains reception, negotiates network or Internet access and securely connects to the proper host before transmitting the PRO data or metadata. Once connected the portable electronic device uploads the subject's entries to one or more questions displayed on the portable electronic device and, optionally, uploads a unique identifier, and downloads any available updated questionnaires. After network activity has concluded, the portable electronic device disconnects from the cellular network, unmounts the device driver and power down the cellular hardware.

The portable electronic device can also be configured to use other network types as well, in which case the procedures can vary slightly, but will follow the same principles as those outlined above.

In embodiments where the portable electronic device transfers the subject's answers immediately or stores them for later transmittal, after it has finished that task, it can again enter a standby state and wait for the next question interrupt.

In one embodiment, a portable electronic device can also, at the instruction of the questionnaire file, set a transmit interrupt. When this interrupt occurs, the portable electronic device can use any of the above methods to connect to the server in question and transfer any answers that have been collected since the previous interrupt and which are residing in the portable electronic device's storage.

Once the questionnaire's pre-programmed routine has completed, the portable electronic device makes a final transmit using the above mechanics, if called for by the questionnaire file, and then goes into a standby mode, awaiting administrative access.

In another embodiment, a portable electronic device can be returned to the facility performing the clinical trial or study. The facility can connect the portable electronic device to a desktop or laptop computer equipped with administrative software that recognizes the portable electronic device. After attaching the portable electronic device to the computer, administrative software on the computer collects any answers remaining on the portable electronic device and optionally removes the previous questionnaire file. The administrative software can also be used to install a new questionnaire file into the portable electronic device in anticipation of its use by a new subject in a new study.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method of clinical trial endpoint development comprising:
   a) administering one or more questions to a subject who is administered a medical product or a placebo, wherein said one or more questions are administered to said subject by a portable electronic device, wherein said device records data about said subject's response to said one or more questions, wherein said one or more questions comprise at least one health-related quality of life (HRQOL) question;
   b) analyzing said data, wherein said analyzing comprises a statistical analysis of responses to said at least one HRQOL question;
   c) developing at least one validated HRQOL question based on said analysis, wherein said developing comprises
      i) determining whether said at least one HRQOL question is an unqualified HRQOL question or a validated HRQOL question based on a capacity of said at least one HRQOL question to serve as an evaluative indicator,
      ii) for said unqualified HRQOL question, revising and/or recreating said unqualified HRQOL question, and repeating steps a) and b); and
      retaining said revised and/or recreated unqualified HRQOL question as a validated HRQOL question based on a capacity of said revised and/or recreated unqualified HRQOL question to serve as an evaluative indicator;
   d) collecting responses from more than one subject administered said validated HRQOL question;
   e) developing one or more clinical trial endpoints based on said responses to said validated HRQOL question; and
   f) assessing a label claim of said medical product tested in a clinical trial comprising said one or more clinical trial endpoints.

2. The method of claim 1, wherein said step a) of administering one or more questions to a subject is part of a pilot trial.

3. The method of claim 1, wherein said analyzing said data is performed on said portable electronic device.

4. The method of claim 1, wherein said analyzing said data comprises sending said data to a data analysis system, wherein said data is analyzed.

5. The method of claim 4, wherein said data is sent to said data analysis system by a wireless connection or wired connection.

6. The method of claim 1, wherein said clinical trial tests said medical product or a placebo on a human subject.

7. The method of claim 1, wherein said analyzing comprises psychometric validation of said data.

8. The method of claim 1, wherein said administering comprises prompting said subject to answer said one or more questions.

9. The method of claim 8, wherein said prompting occurs at a pre-scheduled time or a random time.

10. The method of claim 1, wherein said data comprises information on a time said subject responds to said one or more questions, a date said subject responds to said one or more questions, or a location of said portable electronic device when said subject responds to said one or more questions.

11. The method of claim 1, wherein said analyzing comprises a statistical hypothesis test.

12. The method of claim 11, wherein said statistical hypothesis test is a t-test or a probability value test.

13. The method of claim 1, wherein said data comprises patient-reported outcome (PRO) data or metadata.

14. The method of claim 1, wherein said label claim is an efficacy claim, a safety claim, a toxicity claim, a treatment claim, a health claim, a nutritional claim or a structure/function claim.

15. The method of claim 1, wherein said label claim is reviewed by a regulatory agency.

16. The method of claim 15, wherein said regulatory agency is the United States Food and Drug Administration.

17. The method of claim 1, wherein said medical product is a drug, a biologic, a medical device, a dietary supplement or a cosmetic that is intended to have a human or veterinary use.

18. A computer program product comprising a non-transitory computer readable medium having computer program logic encoded thereon for enabling a processor to develop a clinical trial endpoint comprising:
    a) a receiving procedure that enables a processor to receive data from a portable electronic device, wherein said data comprises a response to one or more questions responded to by a subject who is administered a medical product or a placebo, wherein said one or more questions are administered to said subject by said portable electronic device, wherein said one or more questions comprise at least one health-related quality of life (HRQOL) question;
    b) an analyzing procedure to analyze said data, wherein said analyzing comprises a statistical analysis of responses to said at least one HRQOL question;
    c) a developing procedure to develop at least one validated HRQOL question, wherein said developing comprises
       i) determining whether said at least one HRQOL question is an unqualified HRQOL question or a validated HRQOL question based on a capacity of said at least one HRQOL question to serve as an evaluative indicator,
       ii) for said unqualified HRQOL question, revising and/or recreating said unqualified HRQOL question and repeating a) and b); and
       retaining said revised and/or recreated unqualified HRQOL question as a validated HRQOL question based on a capacity of said revised and/or recreated unqualified HRQOL question to serve as an evaluative indicator;
    d) a collecting procedure for collecting responses from more than one subject administered said validated HRQOL question;
    e) an output procedure to provide one or more clinical trial endpoints based on responses to said validated HRQOL question; and
    f) an assessing procedure for assessing a label claim of said medical product tested in a clinical trial comprising said one or more clinical trial endpoints.

19. The computer program product of claim 18, wherein said data comprises PRO data or metadata.

20. The computer program product of claim 18, wherein said label claim is an efficacy claim, a safety claim, a toxicity claim, a treatment claim, a health claim, a nutritional claim or a structure/function claim.

21. The computer program product of claim 18, where said label claim is reviewed by a regulatory agency.

22. The computer program product of claim 21, wherein said regulatory agency is the United States Food and Drug Administration.

23. The computer program product of claim 18, wherein said medical product is a drug, a biologic, a medical device, a dietary supplement or a cosmetic that is intended to have a human or veterinary use.

24. The computer program product of claim 18, wherein said administering one or more questions to a subject is part of a pilot trial.

25. The computer program product of claim 18, wherein said analyzing said data is performed on said portable electronic device.

26. The computer program product of claim 18, wherein said analyzing said data comprises sending said data to a data analysis system, wherein said data is analyzed.

27. The computer program product of claim 26, wherein said data is sent to said data analysis system by a wireless connection or wired connection.

28. The computer program product of claim 18, wherein said clinical trial tests said medical product or a placebo on a human subject.

29. The computer program product of claim 18, wherein said analyzing comprises psychometric validation of said data.

30. The computer program product of claim 18, wherein said administering comprises prompting said subject to answer said one or more questions.

31. The computer program product of claim 30, wherein said prompting occurs at a pre-scheduled time or a random time.

32. The computer program product of claim 18, wherein said data comprises information on a time said subject responds to said one or more questions, a date said subject responds to said one or more questions, or a location of said portable electronic device when said subject responds to said one or more questions.

33. The computer program product of claim 18, wherein said analyzing comprises a statistical hypothesis test.

34. The computer program product of claim 33, wherein said statistical hypothesis test is a t-test or a probability value test.

35. A computer system for clinical trial endpoint development comprising a non-transitory computer readable medium having computer program logic encoded thereon, wherein said computer program logic comprises instructions, which comprise:
- a) input instructions for receiving data from a portable electronic device, wherein said data comprises a response to one or more questions responded to by a subject who is administered a medical product or a placebo, wherein said one or more questions are administered to said subject by said portable electronic device, wherein said one or more questions comprise at least one health-related quality of life (HRQOL) question;
- b) analysis instructions for analyzing said data, wherein said analyzing comprises a statistical analysis of responses to said at least one HRQOL question;
- c) developing instructions for developing at least one validated HRQOL question, wherein said developing comprises
  - i) determining whether said at least one HRQOL question is an unqualified HRQOL question or a validated HRQOL question based on a capacity of said at least one HRQOL question to serve as an evaluative indicator,
  - ii) for said unqualified HRQOL question, revising and/or recreating said unqualified HRQOL question and repeating execution of a) and b); and
  retaining said revised and/or recreated unqualified HRQOL question as a validated HRQOL question based on a capacity of said revised and/or recreated unqualified HRQOL question to serve as an evaluative indicator;
- d) collecting instructions for collecting responses from more than one subject administered said validated HRQOL question;
- e) output instructions for providing one or more clinical trial endpoints based on said responses to said validated HRQOL question; and
- f) assessing instructions for assessing a label claim of said medical product tested in a clinical trial comprising said one or more clinical trial endpoints.

36. The computer system of claim 35, wherein said data comprises PRO data or metadata.

37. The computer system of claim 35, further comprising instructions to send information to said portable electronic device, wherein said computer system is remote from said portable electronic device.

38. The computer system of claim 37, wherein said information comprises one or more questions.

39. The computer system of claim 35, wherein said label claim is an efficacy claim, a safety claim, a toxicity claim, a treatment claim, a health claim, a nutritional claim or a structure/function claim.

40. The computer system of claim 35, wherein said label claim is reviewed by a regulatory agency.

41. The computer system of claim 40, wherein said regulatory agency is the United States Food and Drug Administration.

42. The computer system of claim 35, wherein said medical product is a drug, a biologic, a medical device, a dietary supplement or a cosmetic that is intended to have a human or veterinary use.

43. The computer system of claim 35, wherein said administering one or more questions to a subject is part of a pilot trial.

44. The computer system of claim 35, wherein said analyzing said data is performed on said portable electronic device.

45. The computer system of claim 35, wherein said analyzing said data comprises sending said data to a data analysis system, wherein said data is analyzed.

46. The computer system of claim 45, wherein said data is sent to said data analysis system by a wireless connection or wired connection.

47. The computer system of claim 35, wherein said clinical trial tests said medical product or a placebo on a human subject.

48. The computer system of claim 35, wherein said analyzing comprises psychometric validation of said data.

49. The computer system of claim 35, wherein said administering comprises prompting said subject to answer said one or more questions.

50. The computer system of claim 49, wherein said prompting occurs at a pre-scheduled time or a random time.

51. The computer system of claim 35, wherein said data comprises information on a time said subject responds to said one or more questions, a date said subject responds to said one or more questions, or a location of said portable electronic device when said subject responds to said one or more questions.

52. The computer system of claim 35, wherein said analyzing comprises a statistical hypothesis test.

53. The computer system of claim 52, wherein said statistical hypothesis test is a t-test or a probability value test.

* * * * *